(12) United States Patent
Kimura et al.

(10) Patent No.: US 11,006,855 B2
(45) Date of Patent: May 18, 2021

(54) HEIGHT MEASURING APPARATUS, HEALTH CARE DEVICE, AND ROTARY GATE

(71) Applicant: RENESAS ELECTRONICS CORPORATION, Tokyo (JP)

(72) Inventors: Kakeru Kimura, Tokyo (JP); Masahito Kajiwara, Tokyo (JP); Shinji Takeda, Tokyo (JP); Takuro Ichikawa, Tokyo (JP); Shoichi Hamada, Tokyo (JP); Koji Hirano, Tokyo (JP)

(73) Assignee: RENESAS ELECTRONICS CORPORATION, Tokyo (JP)

( * ) Notice: Subject to any disclaimer, the term of this patent is extended or adjusted under 35 U.S.C. 154(b) by 270 days.

(21) Appl. No.: 15/970,098

(22) Filed: May 3, 2018

(65) Prior Publication Data

US 2018/0368733 A1   Dec. 27, 2018

(30) Foreign Application Priority Data

Jun. 27, 2017   (JP) .............................. JP2017-124990

(51) Int. Cl.
*A61B 5/107*   (2006.01)
*A61B 5/00*   (2006.01)
*A61B 5/0537*   (2021.01)
*G01B 7/06*   (2006.01)
*G01B 11/06*   (2006.01)

(52) U.S. Cl.
CPC .......... *A61B 5/1072* (2013.01); *A61B 5/0537* (2013.01); *A61B 5/1075* (2013.01); *A61B 5/4869* (2013.01); *G01B 7/082* (2013.01); *A61B 2560/0468* (2013.01); *G01B 11/0608* (2013.01)

(58) Field of Classification Search
CPC ... A61B 5/1072; A61B 5/1075; A61B 5/0537; A61B 5/4869; A61B 2560/0468; G01B 7/082; G01G 19/50
See application file for complete search history.

(56) References Cited

FOREIGN PATENT DOCUMENTS

JP          62-27925 A      2/1987
JP          2001-252258 A   9/2001

*Primary Examiner* — Devin B Henson
*Assistant Examiner* — Joseph A Tombers
(74) *Attorney, Agent, or Firm* — McDermott Will & Emery LLP

(57) ABSTRACT

An ultrasonic receiver receives ultrasonic waves reflected at a plurality of portions of the body of a person to be measured, and thus the person to be measured needs to input the approximate height of himself/herself. An electrostatic capacitance sensor includes a transmission electrode and a reception electrode. The electrostatic capacitance sensor measures a mutual capacitance between the transmission electrode and the reception electrode by a mutual capacitance method. A variable frequency pulse generator generates a pulse supplied to the transmission electrode. A control apparatus allows the variable frequency pulse generator to sweep the frequency of the pulse and allows the electrostatic capacitance sensor to measure the mutual capacitance to identify a frequency at which the measured mutual capacitance is minimized. The control apparatus obtains the height of a person to be measured on the basis of the identified frequency.

15 Claims, 19 Drawing Sheets

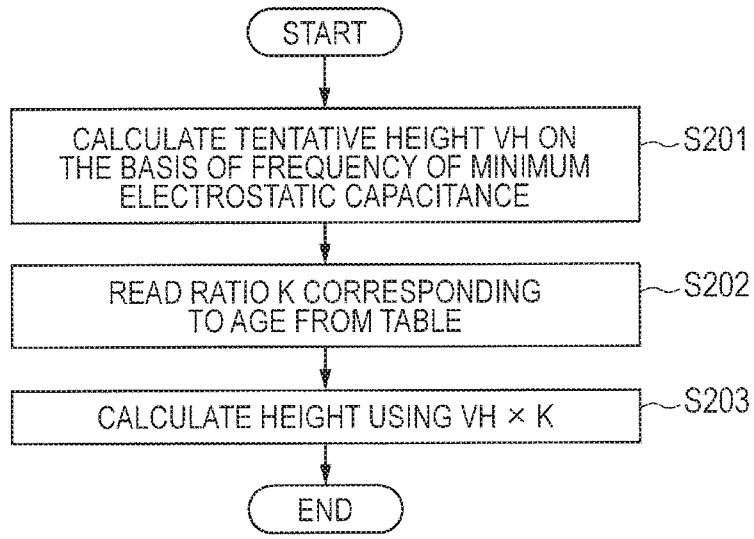
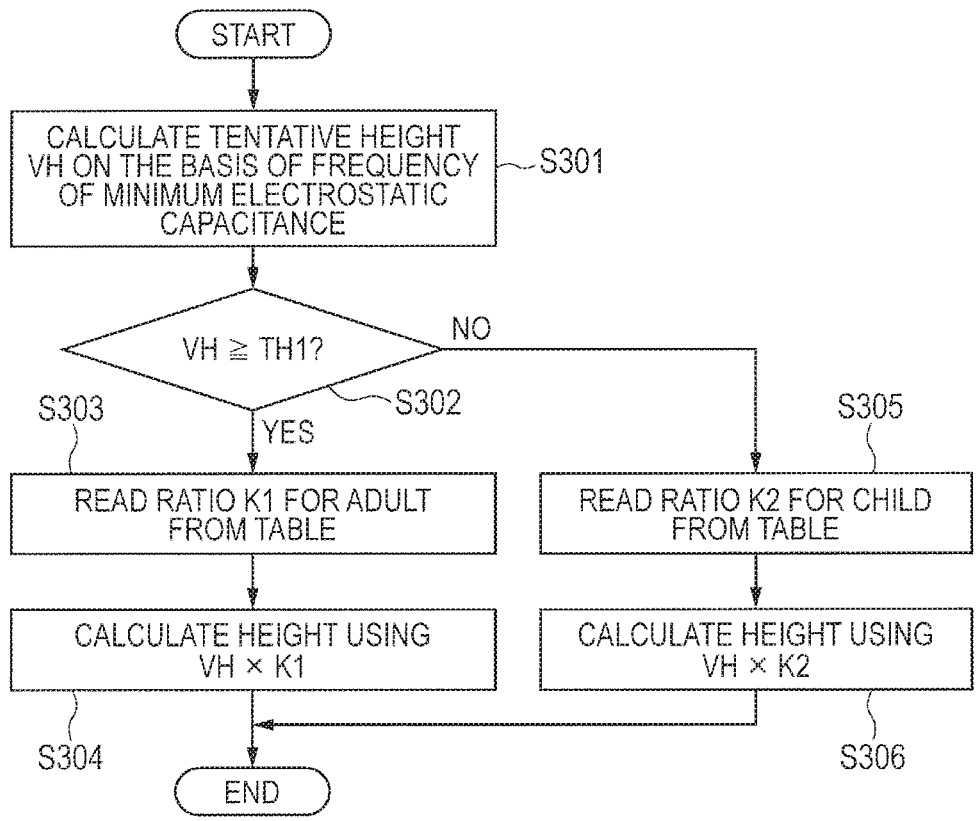

HEIGHT MEASURING APPARATUS, HEALTH CARE DEVICE, AND ROTARY GATE

CROSS-REFERENCE TO RELATED APPLICATIONS

The disclosure of Japanese Patent Application No. 2017-124990 filed on Jun. 27, 2017 including the specification, drawings and abstract is incorporated herein by reference in its entirety.

BACKGROUND

The present invention relates to a height measuring apparatus, a health care device, and a rotary gate, and can be preferably used for, for example, measurement of a height using a sensor.

An apparatus that measures a height using a sensor has been known from the past. For example, each of Japanese Unexamined Patent Application Publication No. 2001-252258 and Japanese Unexamined Patent Application Publication No. SYO 62 (1987)-27925 describes a method of measuring the height of a person to be measured using an ultrasonic sensor including an ultrasonic transmitter and an ultrasonic receiver.

SUMMARY

However, in the height measuring apparatus described in each of Japanese Unexamined Patent Application Publication No. 2001-252258 and Japanese Unexamined Patent Application Publication No. SYO 62 (1987)-27925, the ultrasonic receiver receives ultrasonic waves reflected at a plurality of portions of the body of the person to be measured, and thus the person to be measured needs to input the approximate height of himself/herself.

The other problems and novel features will become apparent from the description of the specification and the accompanying drawings.

A control apparatus of a height measuring apparatus according to an embodiment allows a variable frequency pulse generator to sweep the frequency of a pulse supplied to a transmission electrode and allows an electrostatic capacitance sensor to measure a mutual capacitance between the transmission electrode and a reception electrode to identify a frequency at which the measured mutual capacitance becomes a minimum value, and obtains the height of a person to be measured on the basis of the identified frequency.

According to the embodiment, the height of a person to be measured can be obtained without inputting the approximate height of the person to be measured by himself/herself.

BRIEF DESCRIPTION OF THE DRAWINGS

FIG. 11 is a flowchart for showing a height measuring procedure of a seventh embodiment;

FIG. 12 is a flowchart for showing a height measuring procedure of an eighth embodiment;

DETAILED DESCRIPTION

Hereinafter, embodiments will be described using the drawings. The embodiments will be described while giving the same signs to the same constitutional elements.

First Embodiment

Figure 1:
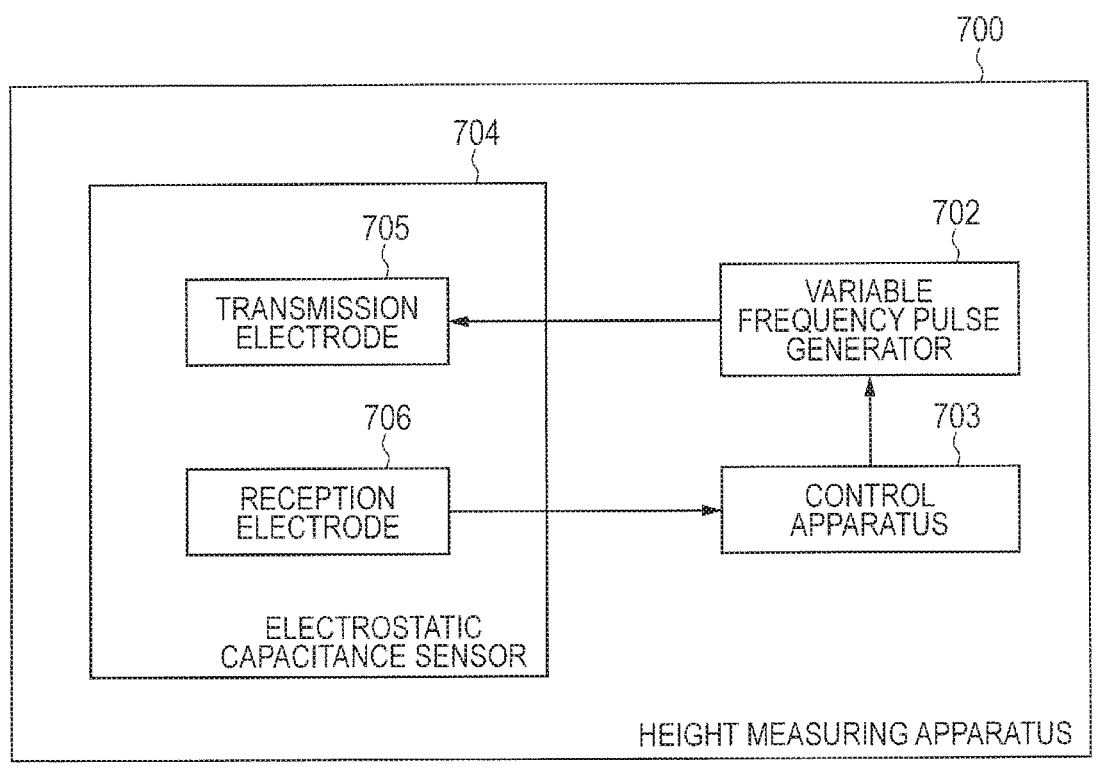
FIG. 1 is a diagram for showing a configuration of a height measuring apparatus of a first embodiment.

FIG. 1 is a diagram for showing a configuration of a height measuring apparatus 700 of a first embodiment.

The height measuring apparatus 700 includes an electrostatic capacitance sensor 704, a variable frequency pulse generator 702, and a control apparatus 703.

The electrostatic capacitance sensor 704 includes a transmission electrode 705 and a reception electrode 706. The electrostatic capacitance sensor 704 measures a mutual capacitance between the transmission electrode and the reception electrode using a mutual capacitance method.

The variable frequency pulse generator 702 generates a pulse supplied to the transmission electrode 705. The control apparatus 703 allows the variable frequency pulse generator 702 to sweep the frequency of the pulse, and allows the electrostatic capacitance sensor 704 to measure the mutual capacitance so that a frequency at which the measured mutual capacitance is minimized is specified. The control apparatus 703 obtains the height of a person to be measured on the basis of the specified frequency.

As described above, according to the embodiment, the height of the person to be measured can be measured by measuring the mutual capacitance between the transmission electrode and the reception electrode using the electrostatic capacitance sensor without inputting the approximate height by himself/herself.

Second Embodiment

Figure 2:
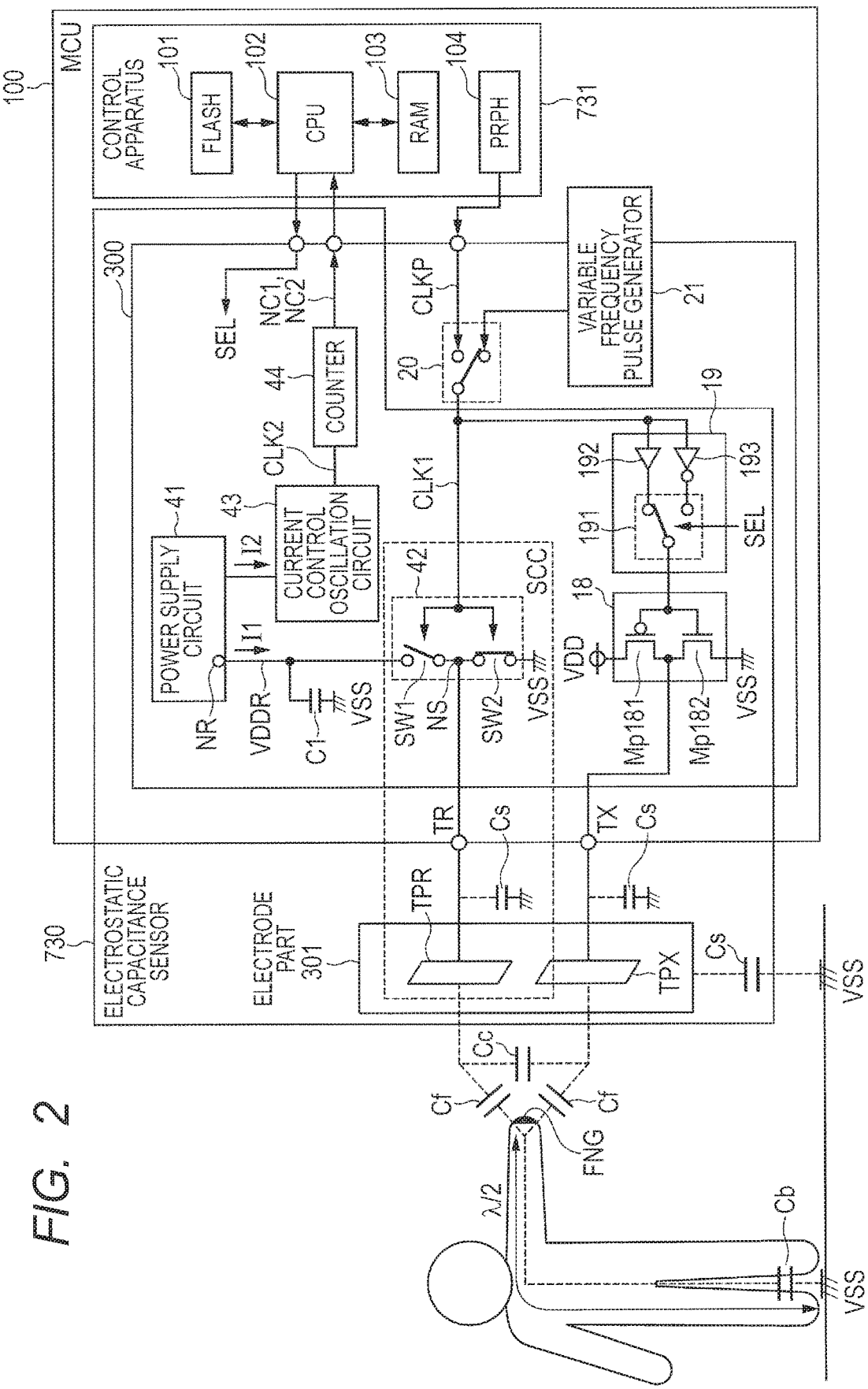
FIG. 2 is a diagram for showing a configuration of a height measuring apparatus of a second embodiment.

FIG. 2 is a diagram for showing a configuration of a height measuring apparatus of a second embodiment.

As shown in FIG. 2, the height measuring apparatus includes an MCU (Micro Controller Unit) 100 and an electrode part 301. The electrode part 301 includes a transmission electrode TPX and a reception electrode TPR. The MCU 100 includes a control apparatus 731, a sensor circuit 300, a terminal TX, and a terminal TR. The control apparatus 731 includes a flash memory 101, a CPU (Central Processing Unit) 102, a RAM (Random Access Memory) 103, and a peripheral circuit (PRPH) 104. The sensor circuit 300 includes a power supply circuit 41, a current control oscillation circuit 43, a counter 44, a switch circuit 42, a phase adjusting circuit 19, an output buffer 18, a variable frequency pulse generator 21, and a switch 20. The electrode part 301, the power supply circuit 41, the current control oscillation circuit 43, the counter 44, the switch circuit 42, the phase adjusting circuit 19, and the output buffer 18 configure an electrostatic capacitance sensor 730.

When a pulse is input to the transmission electrode TPX, an electric field is generated between the transmission electrode TPX and the reception electrode TPR. If a human body (for example, a finger FNG) comes close or comes into contact in this state, a part of the electric field is moved to the human body side, and the electric field between the transmission electrode TPX and the reception electrode TPR is reduced. As a result, a mutual capacitance Cc between the transmission electrode TPX and the reception electrode TPR is reduced. It is possible to detect the human body coming close to or coming into contact with the electrode part 301 by measuring the mutual capacitance Cc using the reception electrode TPR.

The flash memory 101 stores programs, data, and the like used by the CPU 102.

The CPU 102 controls the sensor circuit 300, and obtains the height of a person to be measured on the basis of an output of the sensor circuit 300.

The RAM 103 temporarily stores data and the like necessary for the CPU 102 during the execution of a program.

The PRPH 104 includes an interface circuit for another device, a clock supply source, and the like. The clock supply source included in the PRPH 104 supplies a clock CLK1 to the sensor circuit 300.

The variable frequency pulse generator 21 generates a pulse. The frequency of the pulse can be changed.

The switch 20 selects one of the pulse output from the variable frequency pulse generator 21 and a clock CLKP output from the PRPH 104, and supplies the selected one to the switch circuit 42 and the phase adjusting circuit 19 as the clock CLK1. The switch 20 outputs the pulse as the clock CLK1 in accordance with a switch signal output from the CPU 102 when measuring the height.

The switch circuit 42 applies a power supply voltage VDDR (first power supply voltage) to the terminal TR during the low level of the clock CLK1, and applies a power supply voltage VSS (second power supply voltage, for example, 0V of the ground voltage) to the terminal TR during the high level of the clock CLK1.

The phase adjusting circuit 19 switches so that the phase of the voltage output from the switch circuit 42 is the same as or opposite to that of the voltage output from the output buffer 18 in accordance with a selection signal SEL. A period in which the phase of the voltage output from the switch circuit 42 is the same as that of the voltage output from the output buffer 18 is assumed as an in-phase period, and a period in which the phase of the voltage output from the switch circuit 42 is opposite to that of the voltage output from the output buffer 18 is assumed as an opposite-phase period.

The output buffer 18 applies a power supply voltage VDD (third power supply voltage) to the terminal TX during the low level of the clock CLK1 in the in-phase period, and applies the power supply voltage VSS (second power supply voltage) to the terminal TX during the high level of the clock CLK1. The output buffer 18 applies the power supply voltage VSS (second power supply voltage) to the terminal TX during the low level of the clock CLK1 in the opposite-phase period, and applies the power supply voltage VDD (third power supply voltage) to the terminal TX during the high level of the clock CLK1.

The power supply circuit 41 supplies the power supply voltage VDDR obtained by dropping the power supply voltage VDD to the switch circuit 42. The power supply circuit 41 generates a current I1 to be supplied to the switch circuit 42, and supplies a current I2 equal to a fixed multiple of the current I1 to the current control oscillation circuit 43. The value of the current I1 is changed in response to a change in the mutual capacitance between the transmission electrode TPX and the reception electrode TPR.

The current control oscillation circuit 43 generates a clock CLK2 whose frequency is changed in response to the value of the current I2.

The counter 44 counts the number of clocks CLK2 in the in-phase period, and counts the number of clocks CLK2 in the opposite-phase period. The length of the in-phase period is equal to that of the opposite-phase period.

The CPU 102 calculates a difference value between the count number Nc1 of clocks CLK2 in the in-phase period and the count number Nc2 of clocks CLK2 in the opposite-phase period as a value representing the mutual capacitance between the transmission electrode TPX and the reception electrode TPR. The CPU 102 sweeps the frequency of the pulse output from the variable frequency pulse generator 21, and obtains the height of the person to be measured on the basis of a frequency at which the difference value is minimized.

Figure 3:
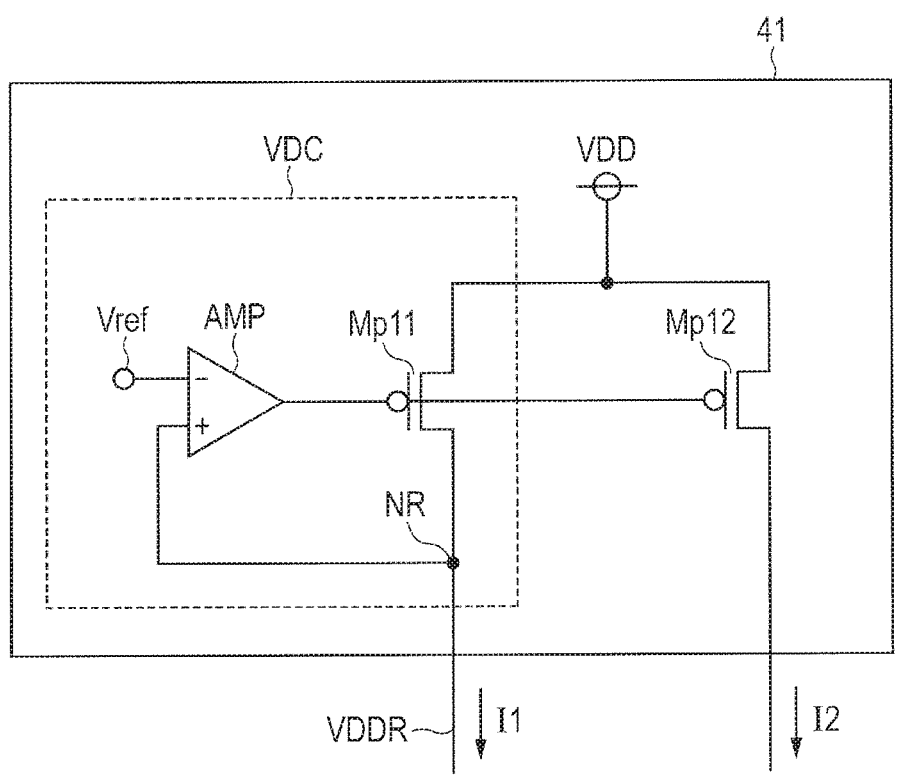
FIG. 3 is a diagram for showing a configuration of a power supply circuit.

FIG. 3 is a diagram for showing a configuration of the power supply circuit 41.

The power supply circuit 41 includes a power supply voltage drop circuit VDC and a P-type transistor Mp12. The power supply voltage drop circuit VDC drops the power supply voltage VDD, and generates the voltage VDDR kept at a desired voltage value to a node NR. A capacitor C1 shown in FIG. 2 is coupled to the node NR in order to suppress the variation of the voltage VDDR.

The power supply voltage drop circuit VDC has a P-type transistor Mp11 and an amplifier AMP. The power supply voltage VDD is applied to the source of the P-type transistor Mp11, and the drain thereof is coupled to the node NR. A reference voltage Vref is applied to one input terminal of the amplifier AMP, and the drain voltage of the P-type transistor Mp11 is applied to the other input terminal through the node NR. The amplifier AMP controls the gate voltage of the P-type transistor Mp11, and generates the voltage VDDR to the node NR so that the drain voltage of the P-type transistor Mp11, namely, the voltage of the node NR is equal to the reference voltage Vref.

The power supply voltage VDD is applied to the source of the P-type transistor Mp12, and the gate thereof is coupled to the gate of the P-type transistor Mp11. Namely, the P-type transistor Mph and the P-type transistor Mp12 form a current mirror circuit. The current mirror circuit generates the current I2 equal to a fixed multiple of the current I1. In the following description, it is assumed that the current I2 equal to the current I1 is generated.

The current driving capability (transistor size) of the P-type transistor Mp11 included in the power supply voltage drop circuit VDC is set so as to be able to supply the current I1 necessary for the switched capacitor circuit SCC. The current driving capability of the P-type transistor Mp12 is set so as to be able to supply the current I2 necessary for the current control oscillation circuit 43.

(Configuration and Operation of Switched Capacitor Circuit SCC)

The switch circuit 42 has a switch SW1 and a switch SW2. One end of the switch SW1 is coupled to the node NR that outputs the voltage VDDR, and the other end thereof is coupled to a node NS. One end of the switch SW2 is coupled to the other end of the switch SW1 through the node NS, and the power supply voltage VSS is applied to the other end of the switch SW2. The conductive states of the switch SW1 and the switch SW2 are complementarily changed in response to the clock CLK1. For example, the switch SW1 is set to the conductive state, and the switch SW2 is set to the non-conductive state in the period of the low level of the clock CLK1.

In the period of the low level of the clock CLK1, the switch SW1 applies the voltage VDDR output from the power supply voltage drop circuit VDC to the terminal TR. In the period of the high level of the clock CLK1, the switch SW2 applies the power supply voltage VSS to the terminal TR. As being apparent from the changes in the logic level of the clock CLK1 and the complementary conductive states (open/close states) of the switch SW1 and the switch SW2, the switch circuit 42 operates in the same manner as a CMOS inverter circuit.

The reception electrode TPR is coupled to the terminal TR. The transmission electrode TPX is coupled to the terminal TX.

Each of the reception electrode TPR and the transmission electrode TPX acts as one electrode of each of a parasitic capacitance Cs and a parasitic capacitance Cf. The other electrode of the parasitic capacitance Cs corresponds to a ground wiring and the like (not shown) of a printed wiring board formed around the reception electrode TPR and the transmission electrode TPX. The other electrode of the parasitic capacitance Cf corresponds to a part (for example, the finger FNG) of the human body of the person to be measured. In addition, the finger FNG acts as one electrode of the parasitic capacitance Cb formed in the human body of the person to be measured. The other electrode of the parasitic capacitance Cb corresponds to a contact face (the ground or the like) between the person to be measured and the ground voltage VSS. Further, a parasitic capacitance Cc of the mutual capacitance is formed between the reception electrode TPR and the transmission electrode TPX.

In the following description, it is assumed that the person to be measured touches the reception electrode TPR and the transmission electrode TPX with the finger FNG. However, the person to be measured may touch the same with a part of the human body such as a palm other than the finger FNG. In addition, the touch includes not only a case in which a part of the human body of the person to be measured comes into contact with the reception electrode TPR and the transmission electrode TPX, but also a case in which a part of the human body does not come into contact therewith but comes close thereto.

The switch circuit 42 and the reception electrode TPR configure the switched capacitor circuit SCC. The switch circuit 42 charges or discharges the parasitic capacitance Cs and the parasitic capacitance Cf formed in the reception electrode TPR in synchronization with the clock CLK1. In the period of the low level of the clock CLK1, the switch circuit 42 applies the voltage VDDR to the reception electrode TPR through the terminal TR to charge the parasitic capacitance Cs and the parasitic capacitance Cf. In the period of the high level of the clock CLK1, the switch circuit 42 applies the power supply voltage VSS to the reception electrode TPR through the terminal TR to discharge the parasitic capacitance Cs and the parasitic capacitance Cf.

(Configuration of Current Control Oscillation Circuit 43 and Counter 44)

The current control oscillation circuit 43 generates the clock CLK2 whose frequency fc2 is changed in accordance with the value of the output current I2 of the power supply circuit 41. As the output current I2 increases, the frequency fc2 of the clock CLK2 increases.

The counter 44 outputs the count number of clocks CLK2 in a count period of time that is appropriately set. The count number of the counter 44 corresponds to an integrated value (namely, the supplied electric charge amount Q) over the count period of time of the current I1 supplied to the switched capacitor circuit SCC.

Figure 4:
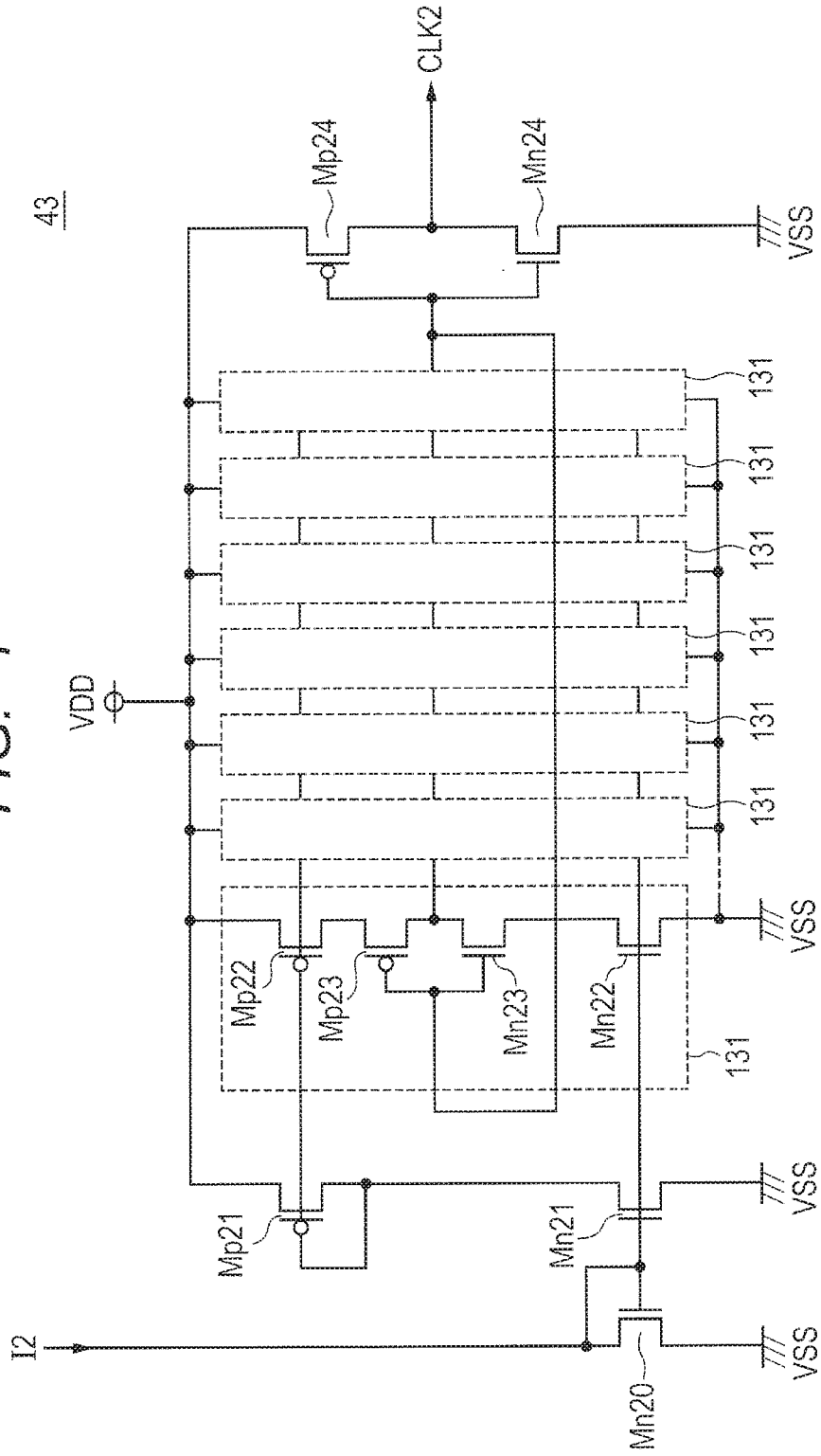
FIG. 4 is a diagram for showing a configuration of a current control oscillation circuit.

FIG. 4 is a diagram for showing a configuration of the current control oscillation circuit 43.

A diode-connected N-type transistor Mn20 draws the current I2 from the drain, and flows out the same from the source to a wiring for the power supply voltage VSS. The gates of the N-type transistor Mn20 and an N-type transistor Mn21 are coupled to each other to form a current mirror circuit. The power supply voltage VDD is applied to the source of a diode-connected P-type transistor Mp21, and the gate and drain thereof are coupled to the drain of the N-type transistor Mn21.

An inverter circuit 131 has P-type transistors Mp22 and Mp23 and N-type transistors Mn22 and Mn23. The power supply voltage VDD is applied to the source of the P-type transistor Mp22, and the drain thereof is coupled to the source of the P-type transistor Mp23. The drain of the P-type transistor Mp23 is coupled to the drain of the N-type transistor Mn23, and the gates of both transistors are coupled to each other. The power supply voltage VSS is applied to the source of the N-type transistor Mn22, and the drain thereof is coupled to the source of the N-type transistor Mn23.

In the inverter circuit 131, the gate of the P-type transistor Mp22 is coupled to the gate of the P-type transistor Mp21, and the gate of the N-type transistor Mn22 is coupled to the gate of the N-type transistor Mn21. Thus, the P-type transistors Mp21 and Mp22 and the N-type transistors Mn21 and Mn22 configure current mirror circuits. Namely, the inverter circuit 131 has a configuration in which a bias current generated on the basis of the current I2 is supplied to the inverter circuit configured using the P-type transistor Mp23 and the N-type transistor Mn23 through the P-type transistor Mp22 and the N-type transistor Mn22. The delay time of the inverter circuit 131 varies depending on the value of the current I2.

The current control oscillation circuit 43 includes ring oscillation circuits obtained by coupling the inverter circuits 131 in a ring shape in a predetermined stages (7 stages in FIG. 4). The inverter circuit configured using a P-type transistor Mp24 and an N-type transistor Mn24 receives an output of the inverter circuit 131 in the last stage of the ring oscillation circuits, and outputs the clock CLK2.

As the value of the current I2 increases, the delay time of the inverter circuit 131 decreases, and the value of the frequency fc2 of the clock CLK2 increases. On the contrary, as the value of the current I2 decreases, the delay time of the inverter circuit 131 increases, and the value of the frequency fc2 decreases.

Figure 5:
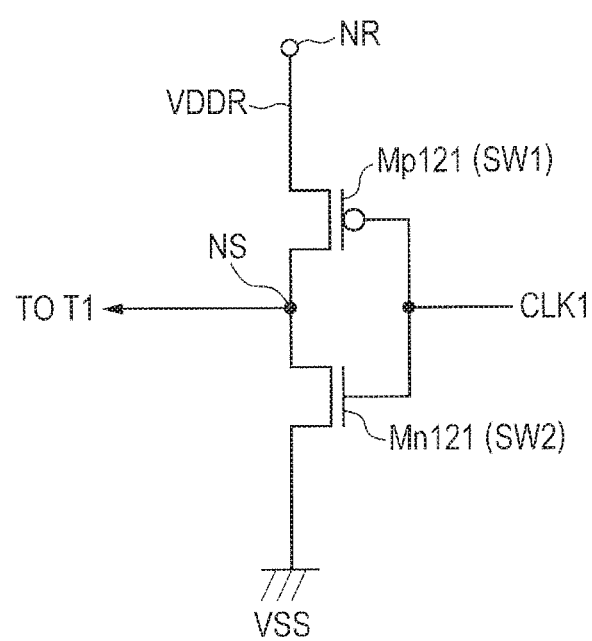
FIG. 5 is a diagram for showing a configuration of a switch circuit.

FIG. 5 is a diagram for showing a configuration of the switch circuit 42.

The switch circuit 42 operates in the same manner as the CMOS inverter circuit as described above. The switch circuit 42 is configured using a general CMOS inverter circuit, and a P-type transistor Mp121 and an N-type transistor Mn121 correspond to the switch SW1 and the switch SW2 in FIG. 2, respectively. The source and drain of the P-type transistor Mp121 are coupled to the node NR and the node NS supplying the voltage VDDR, respectively. The drain and source of the N-type transistor Mn121 are coupled to the node NS and the wiring supplying the power supply voltage VSS, respectively. The clock CLK1 is supplied to the gates of both transistors, and the switch circuit 42 charges or discharges the parasitic capacitance of the reception electrode TPR in response to the logic level of the clock CLK1.

With reference to FIG. 2 again, the phase adjusting circuit 19 has a switch 191, a buffer 192, and an inverter circuit 193. The buffer 192 and the inverter circuit 193 output clocks whose phases are the same as and opposite to the clock CLK1 to the switch 191, respectively. The switch 191 outputs one of the output (whose phase is the same as the clock CLK1) of the buffer 192 and the output (whose phase is opposite to the clock CLK1) of the inverter circuit 193 in response to the logic level of the selection signal SEL.

The switch circuit 42 alternately applies the voltage VDDR and the power supply voltage VSS to the reception electrode TPR through the terminal TR in synchronization with the clock CLK1. The switch circuit 42 applies the low level (power supply voltage VSS) to the terminal TR in the period of the high level of the clock CLK1 to discharge the parasitic capacitance of the reception electrode TPR, and applies the high level (voltage VDDR) to the terminal TR in the period of the low level of the clock CLK1 to charge the parasitic capacitance of the reception electrode TPR.

The output buffer 18 is an inverter circuit configured using a P-type transistor Mp181 to the source of which the power supply voltage VDD is applied and an N-type transistor Mn182 to the source of which the power supply voltage VSS is applied. An output of the phase adjusting circuit 19 is applied to the gates of both transistors, and the drains of both transistors are coupled to the terminal TX.

The output buffer 18 alternately applies the power supply voltage VDD and the power supply voltage VSS to the transmission electrode TPX through the terminal TX in synchronization with the clock CLK1.

The output buffer 18 applies the low level (power supply voltage VSS) to the terminal TX in the period of the high level of the clock CLK1 over a period in which the logic level of the selection signal SEL is set to the low level (power supply voltage VSS), and discharges the parasitic capacitance of the transmission electrode TPX. The output buffer 18 applies the high level (power supply voltage VDD) to the terminal TX in the period of the low level of the clock CLK1 over a period in which the logic level of the selection signal SEL is set to the low level (power supply voltage VSS), and charges the parasitic capacitance of the transmission electrode TPX.

The output buffer 18 applies the high level (power supply voltage VDD) to the terminal TX in the period of the high level of the clock CLK1 over a period in which the logic level of the selection signal SEL is set to the high level (power supply voltage VDD), and charges the parasitic capacitance of the transmission electrode TPX. The output buffer 18 applies the low level (power supply voltage VSS) to the terminal TX in the period of the low level of the clock CLK1 over a period in which the logic level of the selection signal SEL is set to the high level (power supply voltage VDD), and discharges the parasitic capacitance of the transmission electrode TPX.

The selection signal SEL and the voltage level applied to the reception electrode TPR and the transmission electrode TPX are configured as follows. In the period (in-phase period) in which the selection signal SEL is set to one logic level (low level), the voltage level applied to the reception electrode TPR and the transmission electrode TPX is changed to the same phase in synchronization with the clock CLK1. In the period (opposite-phase period) in which the selection signal SEL is set to the other logic level (high level), the voltage level applied to the reception electrode TPR and the transmission electrode TPX is changed to the opposite phase in synchronization with the clock CLK1. The CPU 102 controls so that the length of the in-phase period is equal to that of the opposite-phase period by controlling the logic level of the selection signal SEL.

When the selection signal SEL of the low level is applied to the phase adjusting circuit 19, the voltage waveform applied to the reception electrode TPR and the transmission electrode TPX is changed to the same phase in synchronization with the clock CLK1 (in-phase period). In the in-phase period set to a predetermined period of time (for example, 500 μs), the counter 44 measures the count number Nc1 of clocks CLK2 output from the current control oscillation circuit 43.

In the in-phase period, the timing the switch circuit 42 raises the voltage of the reception electrode TPR from the power supply voltage VSS to the voltage VDDR is nearly equal to the timing the output buffer 18 raises the voltage of the transmission electrode TPX from the power supply voltage VSS to the power supply voltage VDD. In addition, the timing the switch circuit 42 drops the voltage of the reception electrode TPR from the voltage VDDR to the power supply voltage VSS is nearly equal to the timing the output buffer 18 drops the voltage of the transmission electrode TPX from the power supply voltage VDD to the power supply voltage VSS. Namely, the phases of the output waveforms of the switch circuit 42 and the output buffer 18 become the same.

On the other hand, when the selection signal SEL of the high level is applied to the phase adjusting circuit 19, the voltage waveform applied to the reception electrode TPR and the transmission electrode TPX is changed to the opposite phase in synchronization with the clock CLK1 (opposite-phase period). In the opposite-phase period set to 500 μs, the counter 44 measures the count number Nc2 of clocks CLK2.

In the opposite-phase period, the timing the switch circuit 42 raises the voltage of the reception electrode TPR from the power supply voltage VSS to the voltage VDDR is nearly equal to the timing the output buffer 18 drops the voltage of the transmission electrode TPX from the power supply voltage VDD to the power supply voltage VSS. In addition, the timing the switch circuit drops the voltage of the reception electrode TPR from the voltage VDDR to the power supply voltage VSS is nearly equal to the timing the output buffer 18 raises the voltage of the transmission electrode TPX from the power supply voltage VSS to the power supply voltage VDD. Namely, the phases of the output waveforms of the switch circuit 42 and the output buffer 18 become opposite.

(Supplying Electric Charge Amount of Switch Circuit 42)

The parasitic capacitance Cs is formed between the reception electrode TPR and the transmission electrode TPX and the wiring to which the ground voltage VSS is applied. The parasitic capacitance Cf is formed between the reception electrode TPR and the transmission electrode TPX and the finger FNG of the person to be measured. The parasitic capacitance Cc of the mutual capacitance is formed between the reception electrode TPR and the transmission electrode TPX.

An electric charge amount Q1 supplied from the switch circuit 42 in the in-phase period, an electric charge amount Q2 supplied from the switch circuit 42 in the opposite-phase period, and a difference value QS therebetween can be obtained by the following equations (A1), (A2), and (A3).

$$Q1 = (Cs+Cf) \times VDDR + Cc \times (VDDR-VDD) \quad (A1)$$

$$Q2 = (Cs+Cf) \times VDDR + Cc \times (VDDR+VDD) \quad (A2)$$

$$QS = Q2 - Q1 = Cc \times VDD \times 2 \quad (A3)$$

Here, the codes VDDR, VDD, Cs, Cf, and Cc are the values of the voltage VDDR, the power supply voltage VDD, the parasitic capacitance Cs, the parasitic capacitance Cf, and the mutual capacitance Cc.

Q1 is reflected on the count number Nc1 of the counter 44 in the in-phase period. Q2 is reflected on the count number Nc2 of the counter 44 in the opposite-phase period. On the basis of the equation (A3), the difference value obtained by subtracting the count number Nc1 from the count number Nc2 corresponds to a value obtained by reflecting the mutual capacitance Cc between the reception electrode TPR and the transmission electrode TPX.

In the case where the distance between the finger FNG and the reception electrode TPR and the transmission electrode TPX is substantially long (untouched state), the value of the parasitic capacitance Cf between the finger FNG and both electrodes is decreased to an ignorable value with respect to the value of the parasitic capacitance Cc between the reception electrode TPR and the transmission electrode TPX.

On the other hand, in the case where the distance between the finger FNG and the reception electrode TPR and the transmission electrode TPX is short (touched state), the parasitic capacitance Cf cannot be ignored because the number of electric lines of force generated between the finger FNG and the reception electrode TPR and the transmission electrode TPX is increased. In addition, the number of electric lines of force between the reception electrode TPR and the transmission electrode TPX is decreased, and thus the value of the parasitic capacitance Cc between the reception electrode TPR and the transmission electrode TPX becomes smaller than that of the parasitic capacitance Cc in the untouched state. As a result, QS of the equation (3) in the touched state becomes smaller than that in the untouched state.

Thus, when the difference value Qs in the equation (A3) is small, it can be determined as a touched state. When the difference value Qs in the equation (A3) is large, it can be determined as an untouched state. The counter 44 measures the count number in the in-phase period and the opposite-phase period (the same length as the in-phase period).

The CPU 102 calculates a difference value Ns by subtracting the count number Nc1 in the in-phase period from the count number Nc2 in the opposite-phase period. In the touched state, the difference value Ns is small. In the untouched state, the difference value Ns is large. Thus, in the case where the difference value Ns is larger than the reference count number, it can be determined that the finger FNG does not touch. In the case where the difference value Ns is smaller than the reference count number, the finger FNG touches.

Further, the inventors of the application found that when the length half the wavelength of the clock CLK1 (the pulse output from the variable frequency pulse generator 21 when measuring the height) matched the distance from the terminal TR to the ground through the reception electrode TPR and the human body of the person to be measured, the value of the parasitic capacitance Cc between the reception electrode TPR and the transmission electrode TPX was minimized. In the embodiment, the height of the person to be measured is measured using this principle.

Figure 6:
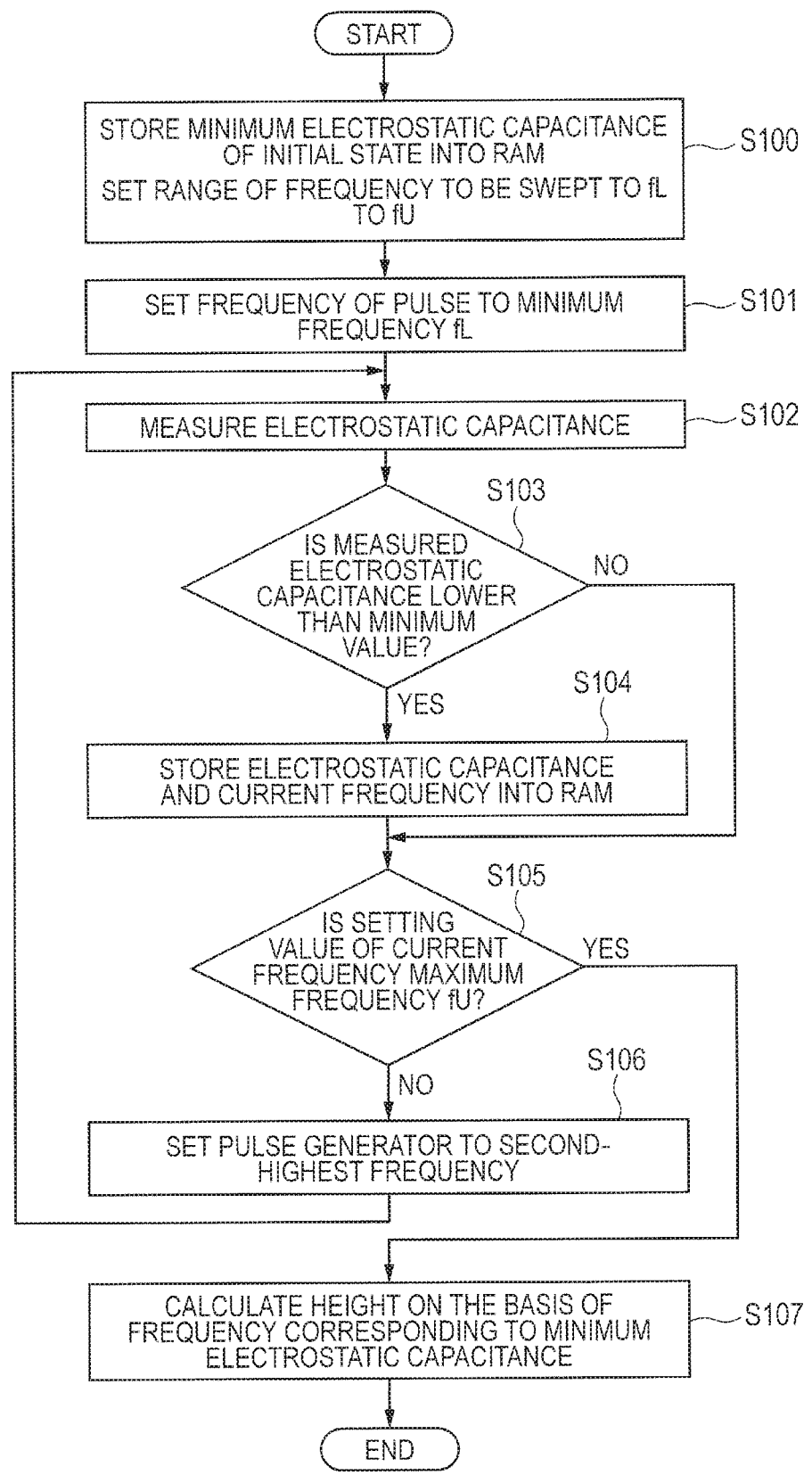
FIG. 6 is a flowchart for showing a height measuring procedure of the second embodiment.

FIG. 6 is a flowchart for showing a height measuring procedure of the second embodiment.

Figure 7:
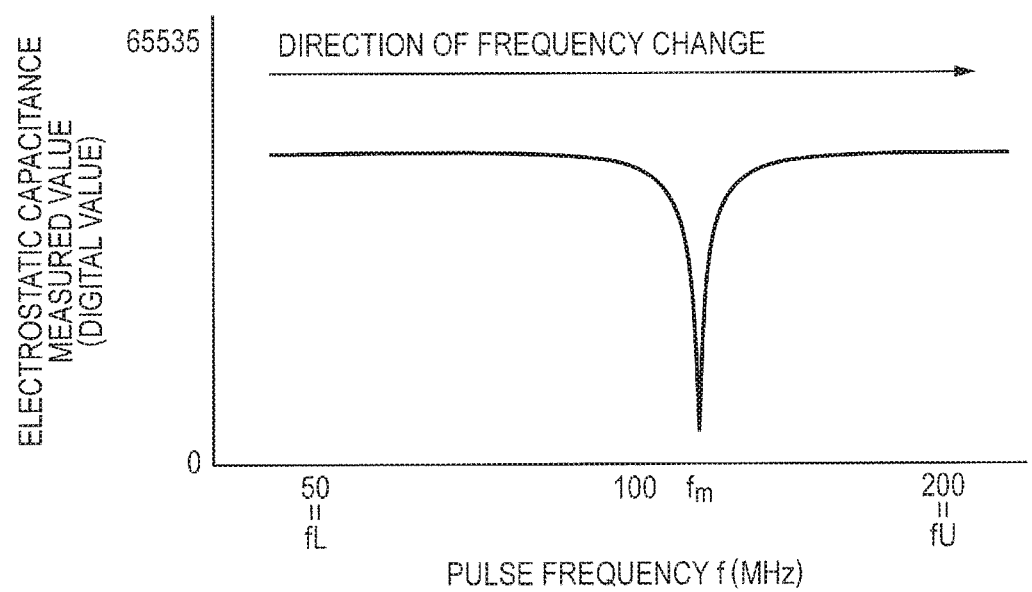
FIG. 7 is a diagram for showing an example of an electrostatic capacitance measured value.

FIG. 7 is a diagram for showing an example of an electrostatic capacitance measured value. The electrostatic capacitance measured value in FIG. 7 is a value representing the mutual capacitance between the reception electrode TPR and the transmission electrode TPX, and is the difference value Ns obtained by subtracting the count number Nc1 in the in-phase period from the count number Nc2 in the opposite-phase period.

With reference to FIG. 6, the CPU 102 stores into the RAM 103 a substantially large value as a minimum electrostatic capacitance measured value MCm of the initial state in Step S100. As shown in FIG. 7, the CPU 102 sets the setting range of the frequency of the pulse to be swept to fL to fU. It is assumed that fL is a frequency corresponding to a length equal to or larger than the maximum value of the height of a person, for example, 3 m. It is assumed that fU is a frequency corresponding to a length equal to or smaller than the minimum value of the height of a person, for example, 75 cm. These values can be calculated by experiment or simulation. For example, fL can be set to 50 MHz, and fU can be set to 75 cm.

In Step S101, the CPU 102 sets the frequency of the pulse generated by the variable frequency pulse generator 21 to the minimum frequency fL within the setting range.

In Step S102, the CPU 102 calculates the difference value Ns of the count number Nc1 in the in-phase period with respect to the count number Nc2 in the opposite-phase period as the electrostatic capacitance measured value MC.

In Step S103, when the electrostatic capacitance measured value MC is smaller than the minimum electrostatic capacitance measured value MCm stored in the RAM 103, the process proceeds to Step S104. When the electrostatic capacitance measured value MC is equal to or larger than the minimum electrostatic capacitance measured value MCm stored in the RAM 103, the process proceeds to Step S105.

In Step S104, the CPU 102 overwrites the electrostatic capacitance measured value MC into the RAM 103 as the minimum electrostatic capacitance measured value MCm, and overwrites the currently-set frequency of the pulse into the RAM 103 as a frequency fm corresponding to the minimum electrostatic capacitance measured value MCm.

In Step S105, in the case where the currently-set frequency of the pulse is a maximum frequency FU within the setting range, the process proceeds to Step S107. In the case where the currently-set frequency of the pulse is not the maximum frequency FU within the setting range, the process proceeds to Step S106.

In Step S106, the frequency of the pulse generated by the variable frequency pulse generator 21 is set to the second-highest frequency within the setting range.

In Step S107, the CPU 102 calculates the height L of the person to be measured on the basis of the equation (A4) using the frequency fm of the pulse corresponding to the minimum electrostatic capacitance measured value MCm stored in the RAM 103. It is assumed that the wavelength of the pulse corresponding to the minimum electrostatic capacitance measured value Mcm is $\lambda$, the wiring length from the terminal TR to the reception electrode TPR is D, and the velocity of light is c.

$$L=\lambda/2-D=c/(2 \times fm)-D \quad (A4)$$

The distance from the terminal TR to the ground through the reception electrode TPR and the human body of the person to be measured corresponds to (L+D).

As described above, the embodiment has the following characteristics.

First, the system of the embodiment can be configured using a circuit having a small scale and a small area as compared to an ultrasonic system. The manufacturing cost can be reduced because the sensor circuit of the electrostatic capacitance sensor is incorporated into the MCU, and the system can be configured using only a substrate on which the MCU and electrode patterns are mounted.

Further, in the embodiment, the height can be calculated with a simple formula using the pulse frequency at which the electrostatic capacitance measured by the electrostatic capacitance sensor is minimized. Thus, the operating time of the CPU can be shortened, and the power consumption can be reduced.

When measuring the electrostatic capacitance, the capacitance Cf between the electrodes TPX and TPR and a part (finger FNG) of the human body of the person to be measured and the parasitic capacitance Cb generated between the finger FNG of the human body and the ground are coupled in series, and are grounded to the ground surface. In general, the parasitic capacitance Cf is up to a few pF, the parasitic capacitance Cb is hundreds of pF, and a relation of Cb>>Cf is satisfied. Accordingly, in the combined capacitance Ct of the parasitic capacitance Cf and the parasitic capacitance Cb coupled in series, the capacitance Cf is dominant, and becomes nearly constant without being influenced by the capacitance Cb. Thus, the influence of the thickness of the shoe sole of the person to be measured and the story of a building can be ignored.

Third Embodiment

In the case where a wiring length D from the terminal TR to the reception electrode TPR can be ignored as compared to the height L of the person to be measured, the CPU 102 may calculate the height L of the person to be measured on the basis of the equation (A5).

$$L=\lambda/2=c/(2 \times fm) \quad (A5)$$

According to the embodiment, in the case where the wiring length D from the terminal TR to the reception electrode TPR can be ignored as compared to the height L of the person to be measured, the height can be obtained much easier.

Fourth Embodiment

The flowchart of FIG. 6 in the second embodiment is based on that the person to be measured touches the electrode part 301 with the human body. However, in the embodiment, the height of the person to be measured is calculated only when the person to be measured touches the electrode part 301 with the human body.

Figure 8:
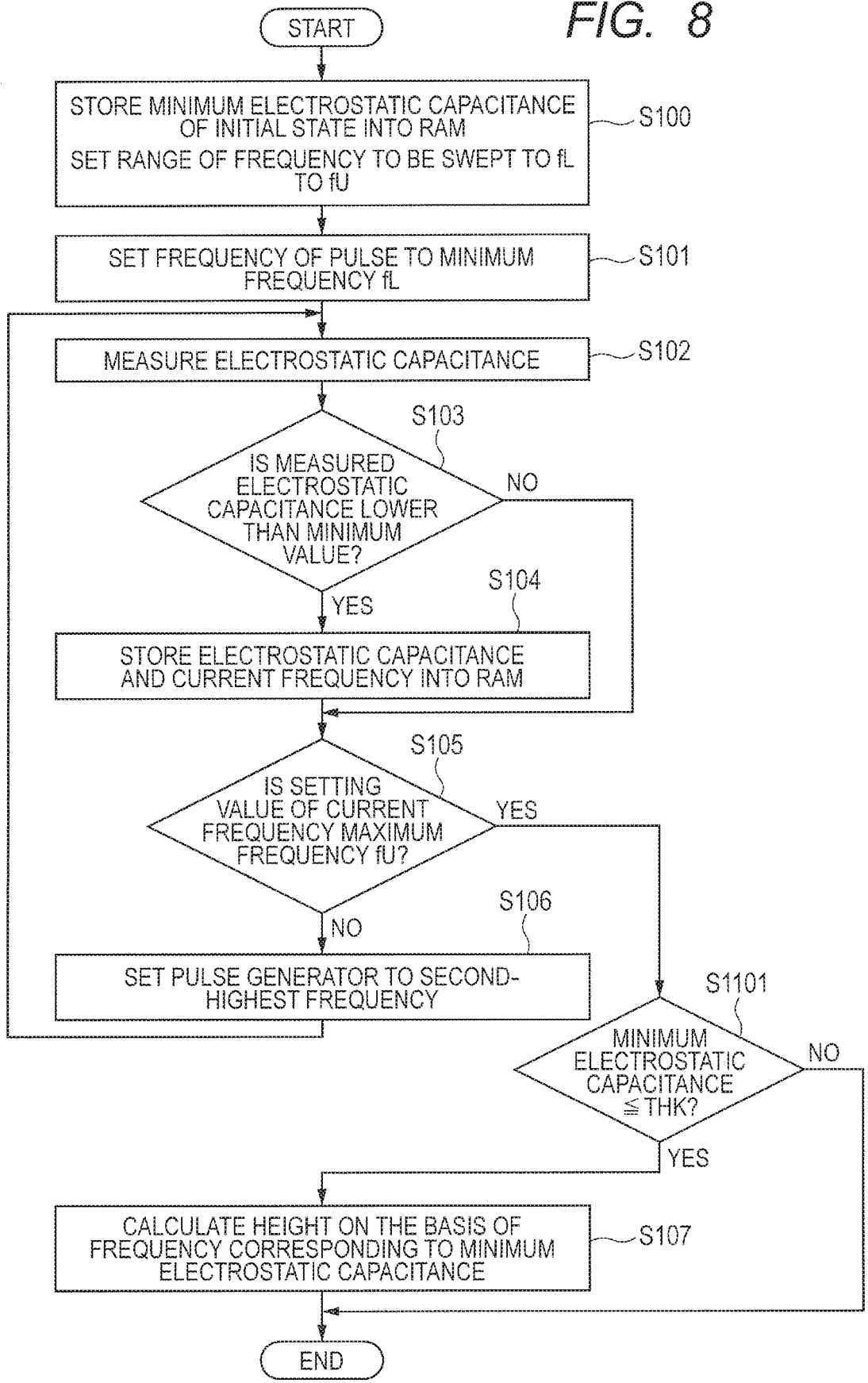
FIG. 8 is a flowchart for showing a height measuring procedure of a fourth embodiment.

FIG. 8 is a flowchart for showing a height measuring procedure of the fourth embodiment.

The flowchart of FIG. 8 is different from that of FIG. 6 in that the flowchart of FIG. 8 includes Step S1101 immediately before Step S107.

In Step S1101, when the minimum electrostatic capacitance measured value MCm is equal to or smaller than a threshold value THX, the process proceeds to Step S107. When the minimum electrostatic capacitance measured value MCm exceeds the threshold value THX, the process is finished. The threshold value THX is a value to determine whether or not the person to be measured has been touching the electrode part 301 with the human body. The threshold value THX is a value larger than the measured value of the electrostatic capacitance when the length half the wavelength of the clock CLK1 matches the distance from the terminal TR to the ground through the reception electrode TPR and the human body of the person to be measured.

The height can be calculated by the above process only when the person to be measured touches the electrode part 301 with the human body.

Fifth Embodiment

Figure 9:
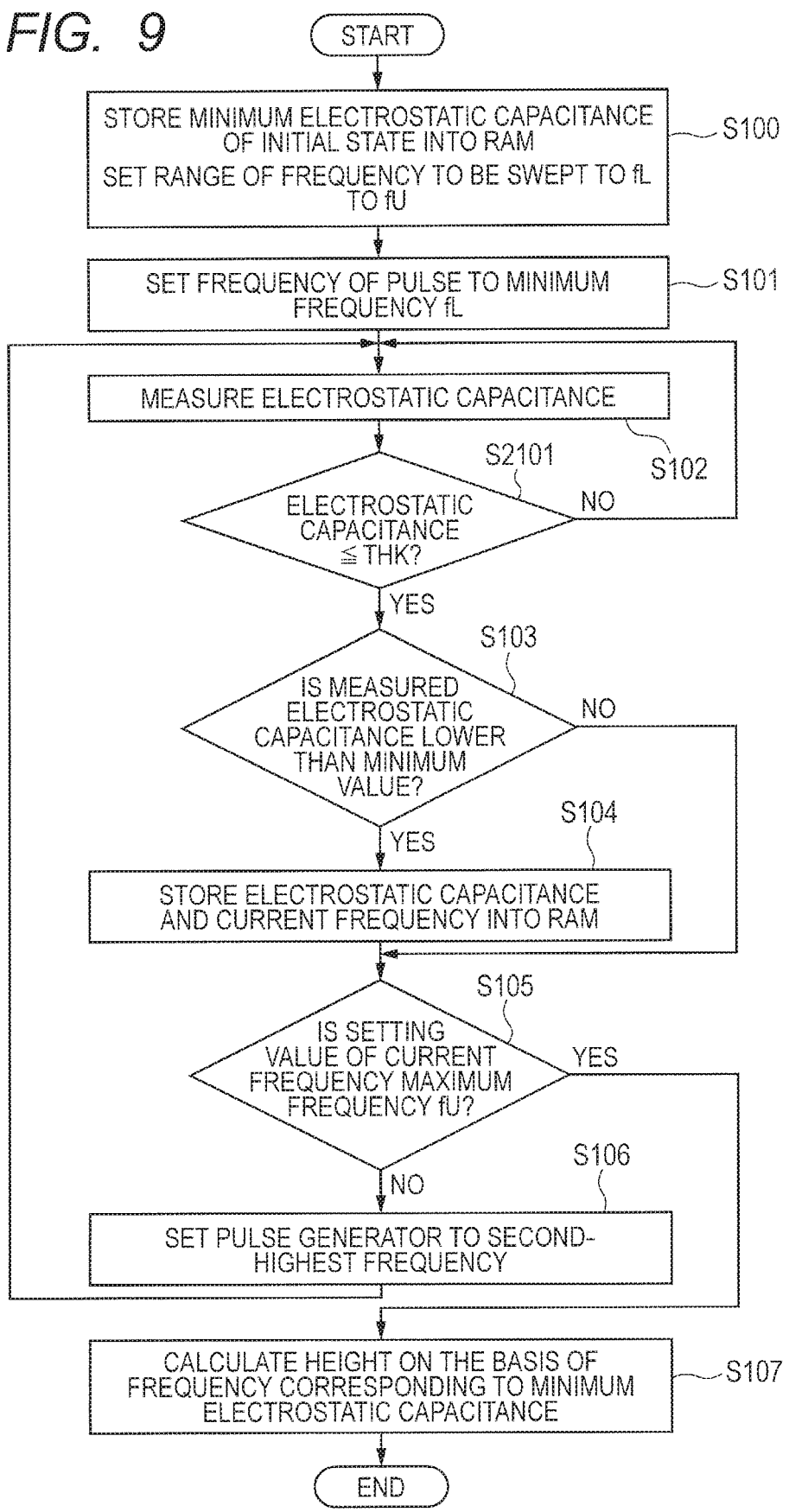
FIG. 9 is a flowchart for showing a height measuring procedure of a fifth embodiment.

FIG. 9 is a flowchart for showing a height measuring procedure of a fifth embodiment.

The flowchart of FIG. 9 is different from that of FIG. 6 in that the flowchart of FIG. 9 includes Step S2101 immediately before Step S103.

In Step S2101, when the electrostatic capacitance measured value MC is equal to or smaller than the threshold value THX, the process proceeds to Step S103. When the electrostatic capacitance measured value MC exceeds the threshold value THX, the process returns to Step S102. The threshold value THX is the same as that in the third embodiment.

The processes (the frequency sweep, the electrostatic capacitance measurement, and the calculation of the height) to obtain the height can be started by the above process only when the person to be measured touches the electrode part 301 with the human body.

Sixth Embodiment

In the second embodiment, when the person to be measured touches the electrode part 301 with a part (the finger FNG or the like) of the human body, the distance from the reception electrode TPR to the contact point between the human body of the person to be measured and the ground is regarded as the height. In the third embodiment, the height of the person to be measured is more precisely measured using a human body ratio.

Figure 10:
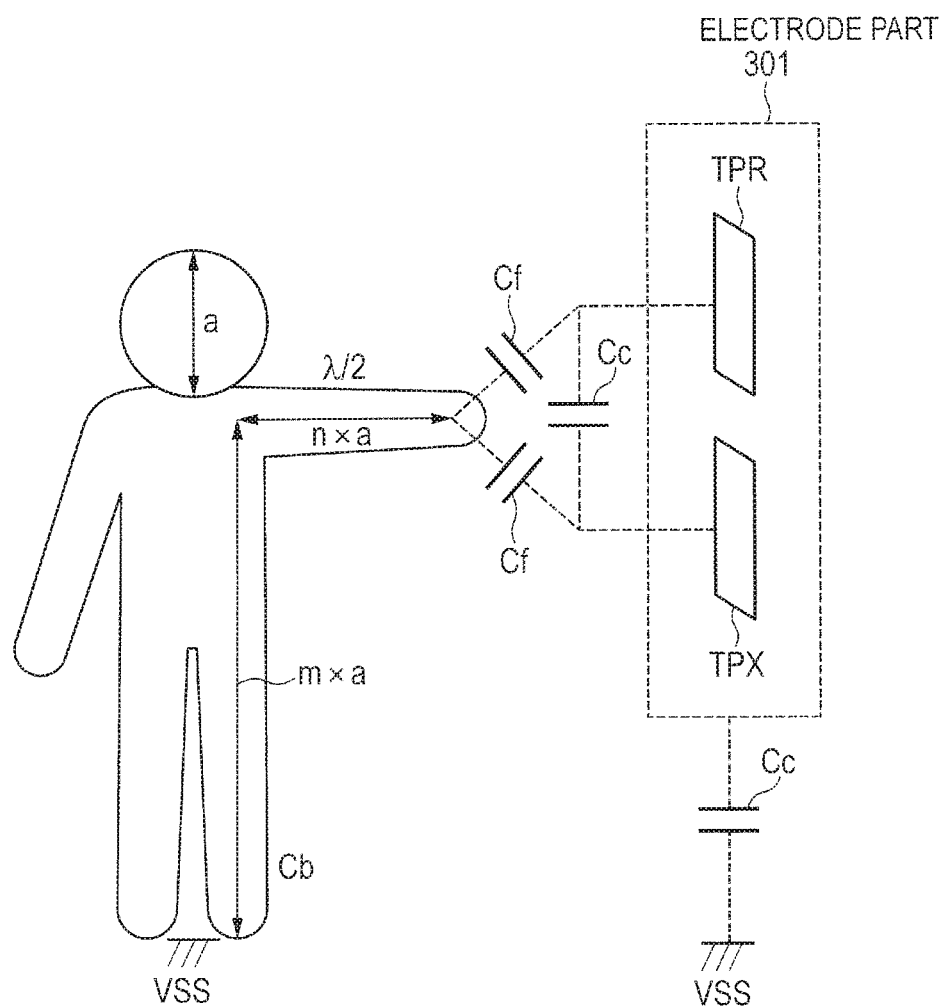
FIG. 10 is a diagram for showing the ratio of each part of a human body.

FIG. 10 is a diagram for showing the ratio of each part of the human body.

When the length of the head is a, the length of the arm can be represented as n×a, and the length of the torso and the leg can be represented as m×a. In this case, the height of the person to be measured is a+ma=(m+1)a, whereas the distance from the reception electrode TPR to the contact point between the human body of the person to be measured and the ground is na+ma=(n+m)a.

The ratio of K=(m+1)/(n+m) is obtained in advance, and can be stored in the flash memory 101. For example, in the case of m=7 and n=3, K is 0.8.

On the assumption that L calculated by the equation (A4) of the second embodiment is a tentative height VH, the CPU 102 can use a value obtained by multiplying the tentative height VH by the ratio K (VH×K) as the height of the person to be measured.

As described above, according to the embodiment, the height can be calculated with a high degree of accuracy by using the human body ratio.

Seventh Embodiment

A height measuring apparatus in the embodiment changes the ratios K according to the ages. The flash memory 101 stores a table in which the ratios K corresponding to the ages are defined. The table may define the ratios for every one year, or may define the ratios for fixed age ranges (every 5 years or 10 years). Alternatively, the table may define a fixed ratio for adults, and may define the ratios for every one year or fixed age ranges only for children.

FIG. 11 is a flowchart for showing a height measuring procedure of the seventh embodiment.

In Step S201, the CPU 102 uses L obtained by the equation (A4) as the tentative height VH by executing Steps S101 to S107 of FIG. 5.

In Step S202, the CPU 102 reads the ratio K corresponding to the age of the person to be measured from the table stored in the flash memory 101.

In Step S203, the CPU 102 multiplies the tentative height VH by the ratio K, and uses the multiplication result as the height of the person to be measured.

As described above, according to the embodiment, the calculation accuracy of the height is increased because the ratios are changed according to the ages.

Eighth Embodiment

A height measuring apparatus in the embodiment determines whether the person to be measured is an adult or a child on the basis of the tentative height obtained by the electrostatic capacitance sensor, and changes the ratio K according to the determination result. The flash memory 101 stores a table in which a ratio K1 for an adult and a ratio K2 for a child are defined.

FIG. 12 is a flowchart for showing a height measuring procedure of the eighth embodiment.

In Step S301, the CPU 102 uses L obtained by the equation (A4) as the tentative height VH by executing Steps S101 to S107 of FIG. 5.

In Step S302, when the tentative height VH is equal to or larger than a threshold value TH1, the process proceeds to Step S303. When the tentative height VH is smaller than the threshold value TH1, the process proceeds to Step S305.

In Step S304, the CPU 102 reads the ratio K1 for an adult from the table stored in the flash memory 101.

In Step S305, the CPU 102 multiplies the tentative height VH by the ratio K1, and uses the multiplication result as the height of the person to be measured.

In Step S306, the CPU 102 reads the ratio K2 for a child from the table stored in the flash memory 101.

In Step S307, the CPU 102 multiplies the tentative height VH by the ratio K2, and uses the multiplication result as the height of the person to be measured.

As described above, according to the embodiment, whether the person to be measured is an adult or a child is determined on the basis of the tentative height, and the ratio K is changed in accordance with the determination result. Thus, it is possible to save time and effort for inputting the age of the person to be measured.

Ninth Embodiment

Figure 13:
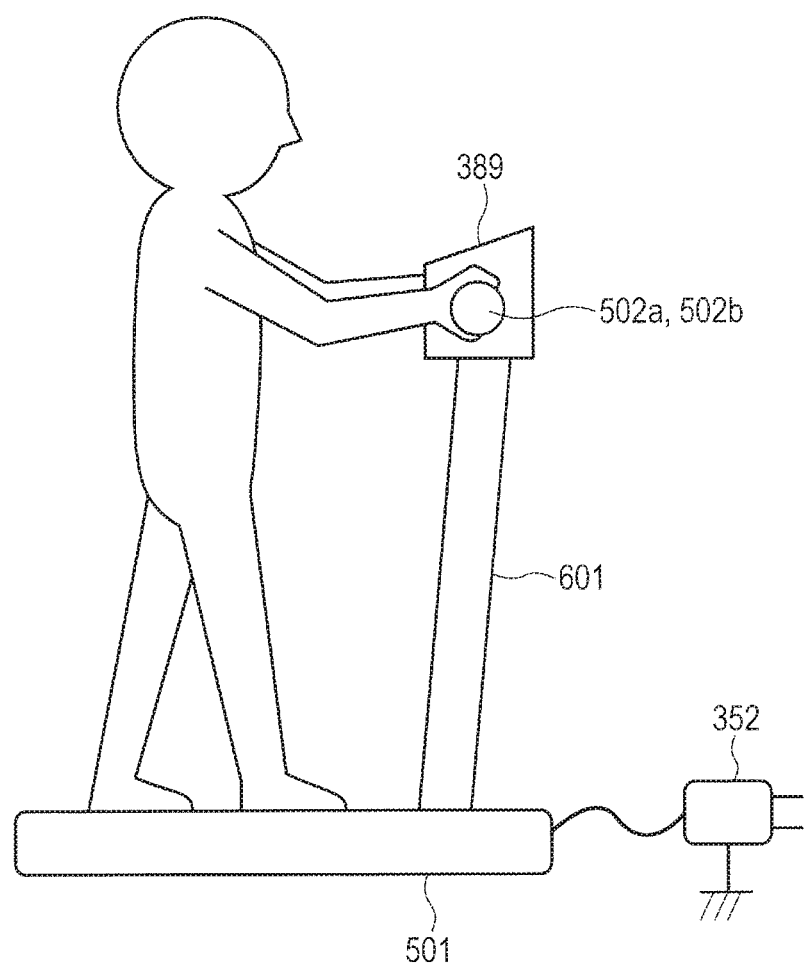
FIG. 13 is a diagram for showing an appearance of a health care device of a ninth embodiment.
Figure 14:
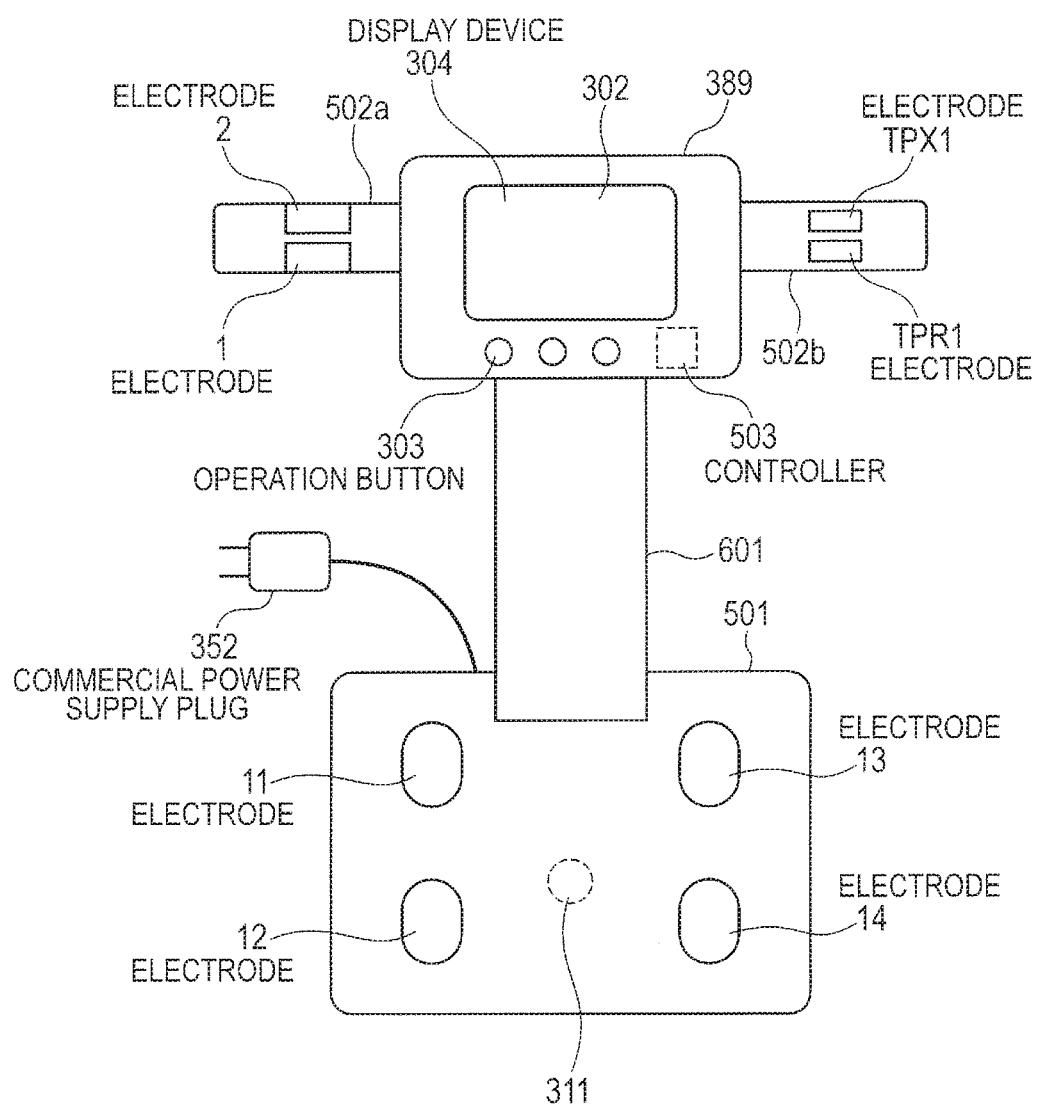
FIG. 14 is a diagram for showing an appearance of the health care device of the ninth embodiment.

FIG. 13 and FIG. 14 are diagrams each showing the appearance of a health care device of a ninth embodiment.

A placement table 501 is configured to be capable of placing the person to be measured.

A console 389 and the placement table 501 are coupled to a support member 601 extending in the vertical direction. The length of the support member 601 is adjusted so that the console 389 is located around the positions of the shoulders of the person to be measured. Alternatively, the console 389 may be movable in the vertical direction in a state where the console 389 is coupled to the support member 601. In addition, a cord that can be wound may be used instead of the support member 601.

A pair of hand grips 502a and 502b is coupled to the console 389 to extend on the left side and right side. The hand grip 502a can be gripped by the left hand of the person to be measured. The hand grip 502b can be gripped by the right hand of the person to be measured.

Figure 15:
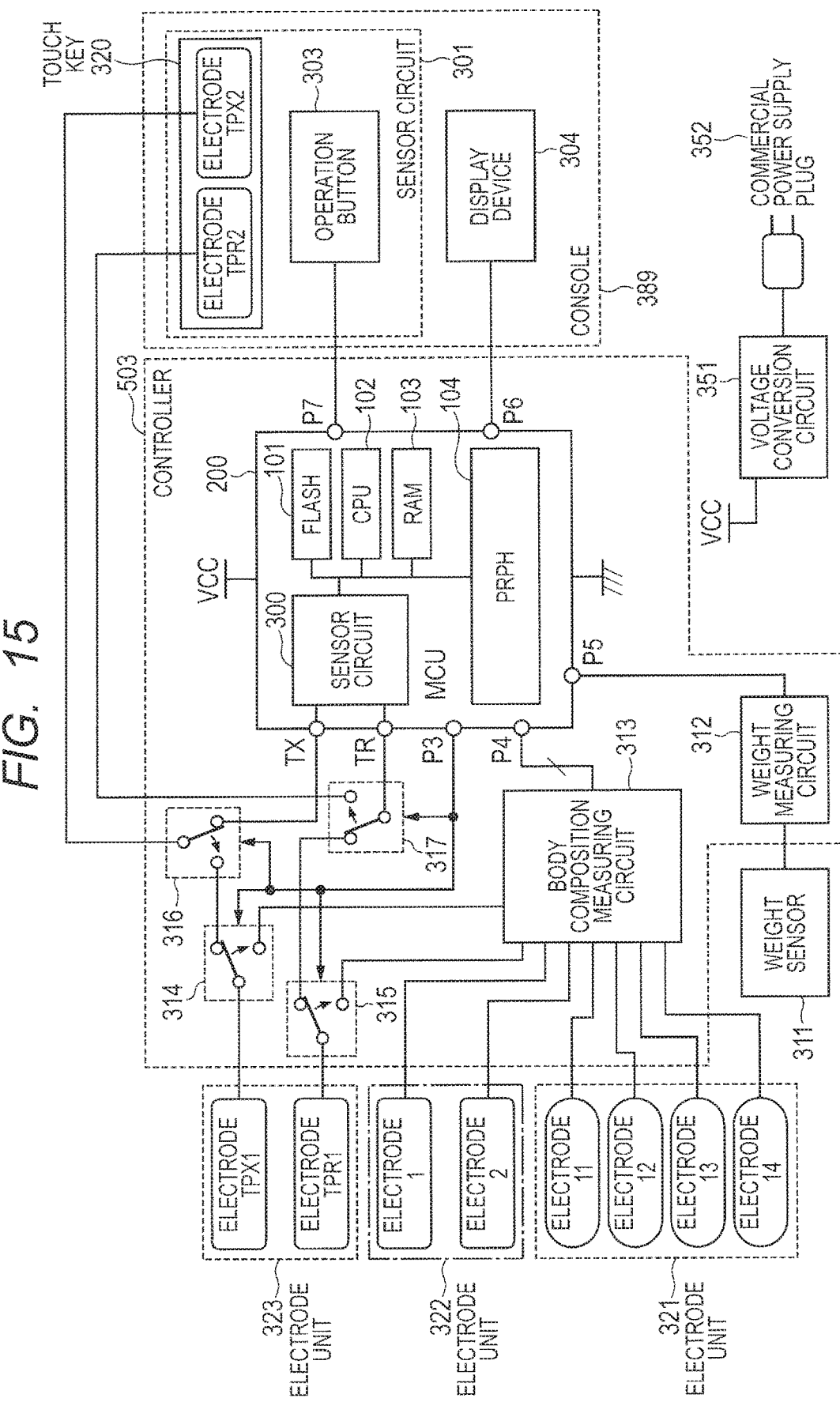
FIG. 15 is a diagram for showing a circuit configuration of the health care device of the ninth embodiment.

FIG. 15 is a diagram for showing a circuit configuration of the health care device of the ninth embodiment.

The health care device includes electrode units 321, 322, and 323, a controller 503, a weight sensor 311, a voltage conversion circuit 351, and the console 389.

The console 389 includes a display device 304, a touch key 320, and an operation button 303. The controller 503 includes an MCU 200, a body composition measuring circuit 313, a weight measuring circuit 312, and switches 314, 315, 316, and 317. As shown in FIG. 14, the controller 503 is provided inside the console 389.

The electrode unit 321 includes an electrode 11, an electrode 12, an electrode 13, and an electrode 14. The electrode 11 functions as a left leg part electrode for body composition measurement in a body composition measuring mode. The electrode 12 functions as a left leg part electrode for body composition measurement in the body composition measuring mode. The electrode 13 functions as a right leg part electrode for body composition measurement in the body composition measuring mode. The electrode 14 functions as a right leg part electrode for body composition measurement in the body composition measuring mode. The electrodes 11 to 14 are coupled to the body composition measuring circuit 313. As shown in FIG. 14, the electrodes 11 to 14 are arranged on the surface of the placement table 501. The electrode 11 is arranged on the left front side of the placement table 501 so as to come into contact with the toe of the left sole of the person to be measured. The electrode 12 is arranged on the left rear side of the placement table 501 so as to come into contact with the heel of the left sole of the person to be measured. The electrode 13 is arranged on the right front side of the placement table 501 so as to come into contact with the toe of the right sole of the person to be measured. The electrode 14 is arranged on the right rear side of the placement table 501 so as to come into contact with the heel of the right sole of the person to be measured.

The electrode unit 322 includes an electrode 1 and an electrode 2. The electrode 1 functions as a left arm part electrode for body composition measurement in the body composition measuring mode. The electrode 2 functions as a left arm part electrode for body composition measurement in the body composition measuring mode. The electrodes 1 and 2 are coupled to the body composition measuring circuit 313. As shown in FIG. 14, the electrodes 1 and 2 are arranged on the surface of the hand grip 502a so as to come into contact with the left hand of the person to be measured.

The electrode unit 323 includes an electrode TPX1 and an electrode TPR1. The electrode TPX1 functions as a transmission electrode of the electrostatic capacitance sensor in a height measuring mode, and functions as a right arm part electrode for body composition measurement in the body composition measuring mode. The electrode TPR1 functions as a reception electrode of the electrostatic capacitance sensor in the height measuring mode, and functions as a left arm part electrode for body composition measurement in the body composition measuring mode. The electrode TPX1 and the electrode TPR1 are configured using a conductor such as metal, and thus can be used as electrodes of the electrostatic capacitance sensor or electrodes of a body composition analyzer. As shown in FIG. 14, the electrodes TPX1 and TPR1 are arranged on the surface of the hand grip 502b so as to come into contact with the right hand of the person to be measured.

The weight sensor 311 is incorporated near the center of the placement table 501.

The voltage conversion circuit 351 converts a commercial power supply voltage supplied from a commercial power supply plug 352 into a power supply voltage VCC to be supplied to the MCU 200.

The display device 304 displays a height measurement result, a body composition measurement result, a weight measurement result, a BMI measurement result, and the like.

The touch key 320 includes an electrode TPX2 and an electrode TPR2. The sensor circuit 300 detects that the human body of the person to be measured comes close to or comes into contact with the electrode TPX2 and the electrode TPR2, so that the CPU 102 switches the operation input mode, the height measuring mode, and the body composition mode. After the height measuring mode is selected, the CPU 102 returns the height measuring mode to the operation input mode after the height measurement is completed. After the body composition measuring mode is selected, the CPU 102 returns the body composition measuring mode to the operation input mode after the body composition measurement is completed.

The MCU 200 includes the flash memory 101, the CPU 102, the RAM 103, the PRPH 104, the sensor circuit 300, the terminal TR, and the terminal TX as similar to the MCU 100 illustrated in FIG. 2.

The MCU 200 further includes terminals P3, P4, P5, P6, and P7.

The body composition measuring circuit 313 measures the body composition, and outputs data representing the body composition to the terminal P4 of the MCU 200.

The weight measuring circuit 312 calculates the weight of the person to be measured in accordance with an output signal of the weight sensor 311, and outputs the same to the terminal P5 of the MCU 200.

The switch 314 switches the coupling destination of the electrode TPX1 to the switch 316 or the body composition measuring circuit 313. The switch 314 couples the electrode TPX1 and the switch 316 to each other in the height measuring mode, and couples the electrode TPX1 and the body composition measuring circuit 313 to each other in the body composition measuring mode.

The switch 315 switches the coupling destination of the electrode TPR1 to the switch 317 or the body composition measuring circuit 313. The switch 315 couples the electrode TPR1 and the switch 317 to each other in the height measuring mode, and couples the electrode TPR1 and the body composition measuring circuit 313 to each other in the body composition measuring mode.

The switch 316 switches the coupling destination of the terminal TX to the switch 314 or the electrode TPX2. The switch 316 couples the terminal TX and the switch 314 to each other in the height measuring mode, and couples the terminal TX and the electrode TPX2 to each other in the operation input mode.

The switch 317 switches the coupling destination of the terminal TR to the switch 315 or the electrode TPR2. The switch 317 couples the terminal TR and the switch 315 to each other in the height measuring mode, and couples the terminal TR and the electrode TPR2 to each other in the operation input mode.

The terminal P3 is coupled to the switches 314, 315, 316, and 317. The CPU 102 outputs a switch signal to the switches 314, 315, 316, and 317 through the terminal P3.

The terminal P4 is coupled to the body composition measuring circuit 313.

The terminal P5 is coupled to the weight measuring circuit 312.

The terminal P6 is coupled to the display device 304.

The terminal P7 is coupled to the operation button 303.

The body composition measuring circuit 313 measures the body composition of the human body of the person to be measured using a biological impedance method or the like. The body composition to be measured includes at least one of a body fat percentage, a muscle percentage, a fat removal quantity, a body fat quantity, and a muscle quantity.

The body composition measuring circuit 313 uses two of the electrodes 1, 2, 11, 12, 13, 14, TPX1, and TPR1 as electrodes for applying a current to the human body of the person to be measured, and uses other two thereof as electrodes for measuring a voltage. Accordingly, the body composition of a part of the human body of the person to be measured is measured.

For example, the body composition measuring circuit 313 uses the electrode 1 (the left arm part) and the electrode 11 (the left leg part) as electrodes for applying a weak current to the human body of the person to be measured, and uses the electrode 2 (the left arm part) and the electrode 12 (the left leg part) as electrodes for measuring a voltage. Accordingly, the body composition of the left side of the body of the person to be measured is estimated. The body composition measuring circuit 313 uses the electrode TPR1 (the right arm part) and the electrode 13 (the right leg part) as electrodes for applying a weak current to the human body of the person to be measured, and uses the electrode TPX1 (the right arm part) and the electrode 14 (the right leg part) as electrodes for measuring a voltage. Accordingly, the body composition of the right side of the body of the person to be measured is measured. The body composition measuring circuit 313 uses the electrode 1 (the left arm part) and the electrode TPR1 (the right arm part) as electrodes for applying a weak current to the human body of the person to be measured, and uses the electrode 2 (the left arm part) and the electrode TPX1 (the right arm part) as electrodes for measuring a voltage. Accordingly, the body composition between both arms of the person to be measured is measured. The body composition measuring circuit 313 uses the electrode 11 (the left leg part) and the electrode 13 (the right leg part) as electrodes for applying a weak current to the human body of the person to be measured, and uses the electrode 12 (the left leg part) and the electrode 14 (the right leg part) as electrodes for measuring a voltage. Accordingly, the body composition between both legs of the person to be measured is measured.

The body composition is measured by changing a combination of two electrodes for applying a current and two electrodes for applying a voltage, and the measurement result is added or subtracted, so that the body composition for each part of the human body of the person to be measured and the body composition of the entire human body can be obtained.

The CPU 102 obtains the BMI (Body Mass Index) of the person to be measured on the basis of the measured height and weight of the person to be measured. When the weight of the person to be measured is W(kg) and the height thereof is M(m), the BMI can be obtained using $W/M^2$.

Figure 16:
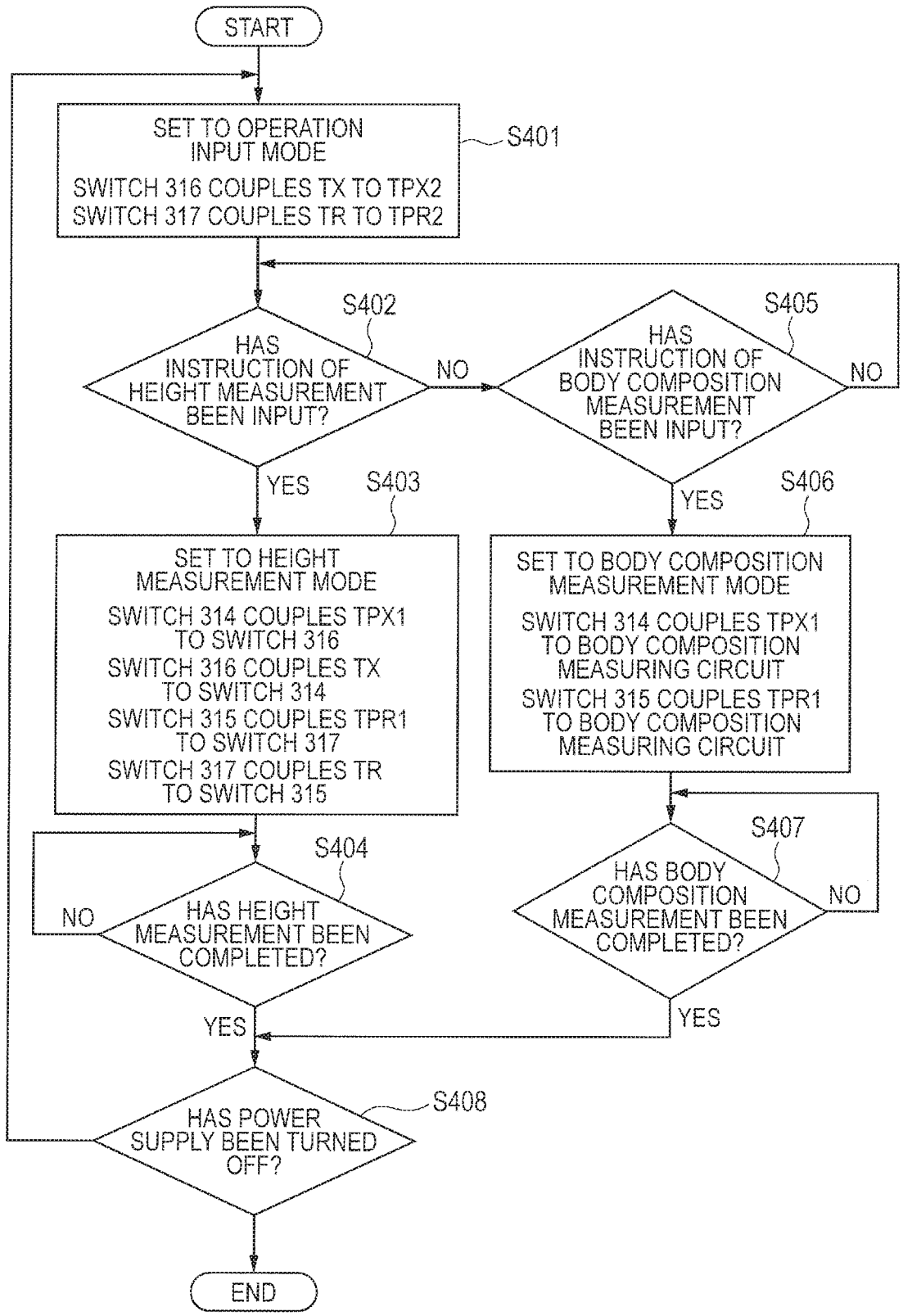
FIG. 16 is a flowchart for showing a control procedure of switches in the health care device of the ninth embodiment.

FIG. 16 is a flowchart for showing a control procedure of the switches in the health care device of the ninth embodiment.

In Step S401, the CPU 102 sets the current mode to the operation input mode. The CPU 102 sets the switch 316 so as to couple the terminal TX to the electrode TPX2. The CPU 102 sets the switch 317 so as to couple the terminal TR to the electrode TPR2.

In Step S402, in the case where an instruction of height measurement has been input through the touch key 320, the process proceeds to Step S403. For example, when the electrostatic capacitance sensor detects that a part of the human body of the person to be measured has come into contact with the electrode TPX2 and the electrode TPR2 once, the CPU 102 may determine that the instruction of height measurement has been input.

In Step S403, the CPU 102 sets the current mode to the height measuring mode. The CPU 102 sets the switch 314 so as to couple the electrode TPX1 to the switch 316. The CPU 102 sets the switch 315 so as to couple the electrode TPR1 to the switch 317. The CPU 102 sets the switch 316 so as to couple the terminal TX to the switch 314. The CPU 102 sets the switch 317 so as to couple the terminal TR to the switch 315.

In Step S405, in the case where an instruction of body composition measurement has been input through the touch key 320, the process proceeds to Step S406. For example, when the electrostatic capacitance sensor detects that a part of the human body of the person to be measured has come into contact with the electrode TPX2 and the electrode TPR2 twice in a row, the CPU 102 may determine that the instruction of body composition measurement has been input.

In Step S404, in the case where the height measurement has been completed, the process proceeds to Step S408.

In Step S406, the CPU 102 sets the current mode to the body composition measuring mode. The CPU 102 sets the switch 314 so as to couple the electrode TPX1 to the body composition measuring circuit 313. The CPU 102 sets the switch 315 so as to couple the electrode TPR1 to the body composition measuring circuit 313.

In Step S407, in the case where the body composition measurement has been completed, the process proceeds to Step S408.

In Step S408, the power supply is not turned off, the process returns to Step S401.

A health care device for measuring the body composition in the related art could not measure the height. Therefore, it was necessary for the person to be measured to measure the height with a height meter or the like, and then to input the measured height through an operation panel. According to the health care device of the embodiment, since the height can be measured in addition to the body composition, it is possible to save time and effort for measuring the height with a height meter and inputting the height.

It should be noted that in order to enhance the accuracy of the height measurement, there is a method in which the measurement result is averaged by increasing the number of times of scanning of the frequency. The body composition measurement requires a relatively long time such as a few seconds to several tens of seconds. Accordingly, even if the scanning of the frequency for the height measurement is performed a few times, the time required for the height measurement is shorter than that required for the body composition measurement. Thus, even if the scanning of the frequency for the height measurement is performed a few times, the person to be measured does not feel the measurement time long.

Modified Example of Ninth Embodiment

In the ninth embodiment, the touch key 320 includes a set of the transmission electrode and the reception electrode. However, the touch key 320 may include a plurality of sets of the transmission electrodes and the reception electrodes. The person to be measured can recognize a touched position by arranging each set of the transmission electrode and the reception electrode at different positions. The CPU may switch to a mode in accordance with the position touched by the person to be measured.

Tenth Embodiment

Figure 17:
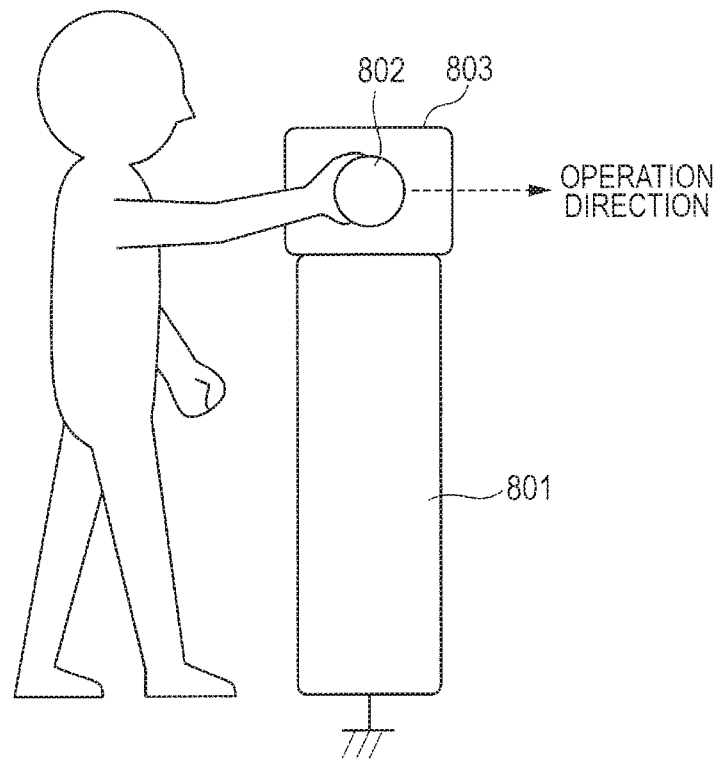
FIG. 17 is a diagram for showing a rotary gate incorporating a height measurement function of a tenth embodiment.
Figure 18:
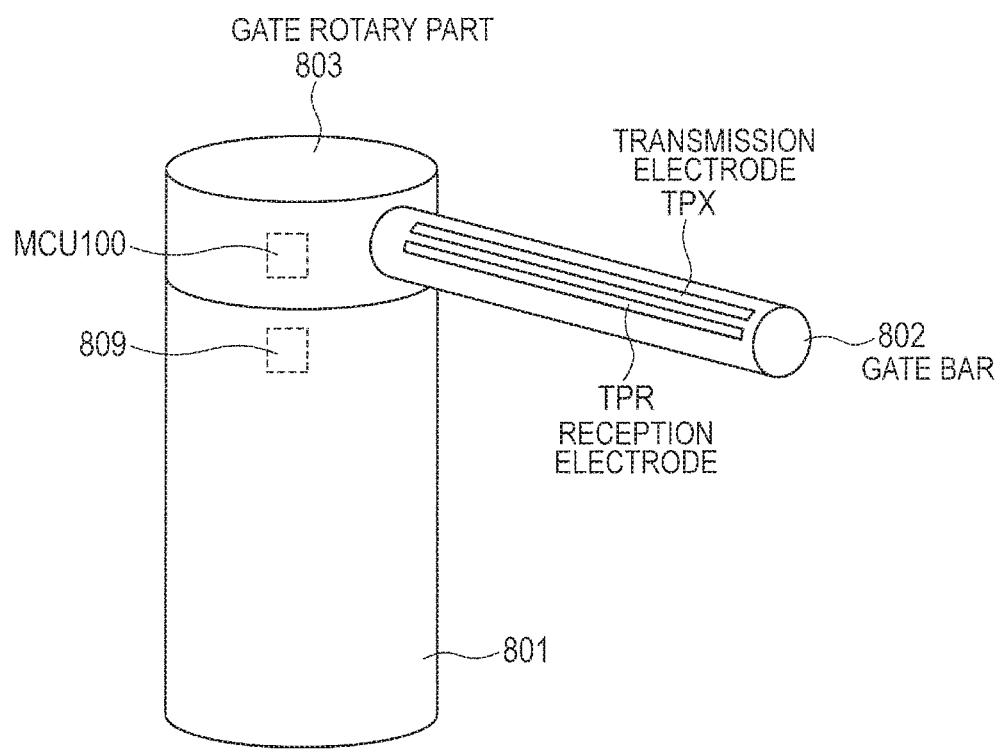
FIG. 18 is a diagram for showing the rotary gate incorporating the height measurement function of the tenth embodiment.

FIG. 17 and FIG. 18 are diagrams each showing a rotary gate incorporating a height measurement function of a tenth embodiment.

The rotary gate is provided at an entry gate to a facility or the like. The rotary gate includes a support pole 801, a gate rotary part 803, a gate bar 802 that is movable in a rotatable manner, and a driving unit 809.

The gate rotary part 803 is rotatably attached to the upper surface of the support pole 801.

The gate bar 802 is attached to the gate rotary part 803, and is rotated in association with the rotation of the gate rotary part 803.

The driving unit 809 allows the gate rotary part 803 to rotate in accordance with an instruction of the CPU 102 in FIG. 2.

The transmission electrode TPX and the reception electrode TRX of FIG. 2 are arranged on the surface of the gate bar 802.

The MCU 100 of FIG. 2 is provided inside the gate rotary part 803.

When a visitor pushes the gate bar 802 of the rotary gate with his/her hand at the walking speed, the height is measured by the electrodes TPX and TPR attached to the gate bar 802 and the MCU 100. In the case where the measured height falls within an allowable range, the gate rotary part 803 is rotated by the driving unit 809 to rotate the gate bar 802. Thus, the visitor can enter the facility.

Figure 19:
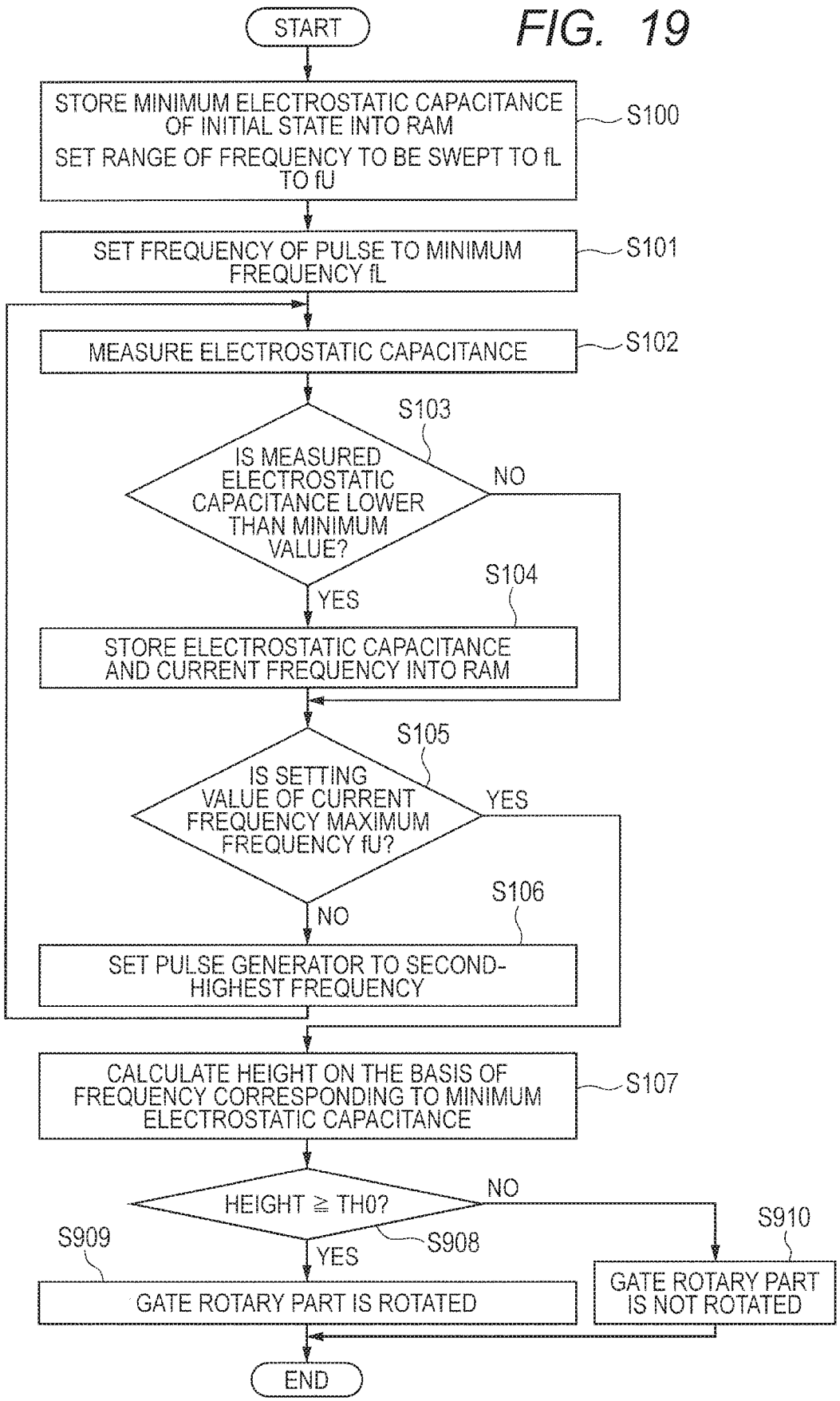
FIG. 19 is a flowchart for showing a control procedure of the rotary gate of the tenth embodiment.

FIG. 19 is a flowchart for showing a control procedure of the rotary gate of the tenth embodiment.

The flowchart of FIG. 19 includes S908 to S910 in addition to S101 to S105 of the flowchart of FIG. 6.

After the calculation of the height in Step S107, in the case where the height is equal to or larger than a threshold value TH0 in Step S108, the process proceeds to Step S909. In the case where the height is smaller than the threshold value TH0, the process proceeds to Step S910.

In Step S909, the CPU 102 allows the driving unit 809 to rotate the gate rotary part 803 so that the gate bar 802 is rotated.

In Step S910, the CPU 102 does not allow the driving unit 809 to rotate the gate rotary part 803. Accordingly, the gate bar 802 is not rotated.

In the past, an attendant visually checked the height of a visitor, and permitted the visitor to enter in the case where the height was equal to or larger than the limit height. Thus, there were problems of congestion of the facility and delay in start time. As in the embodiment, the entrance can be efficiently controlled by the gate management provided with the height measurement function. Since the measurement of the height is completed in a period of time sufficiently shorter than that in which the gate is continuously pushed, it is highly possible to notify by controlling opening/closing of the gate after the completion of the measurement.

Eleventh Embodiment

A period of time during which a visitor touches the gate bar 802 with his/her hands is relatively short. Therefore, it is necessary to measure the height in a short time.

In the embodiment, the CPU 102 sweeps the range of the frequency smaller than the limit height. In the case where there is a frequency at which the measured mutual capacitance is equal to or smaller than a threshold value THY in the range of the swept frequency, the CPU 102 determines that the height of the person to be measured is smaller than the limit height. In the case where there is not a frequency at which the measured mutual capacitance is equal to or smaller than the threshold value THY in the range of the swept frequency, the CPU 102 determines that the height of the person to be measured is equal to or larger than the limit height.

Figure 20:
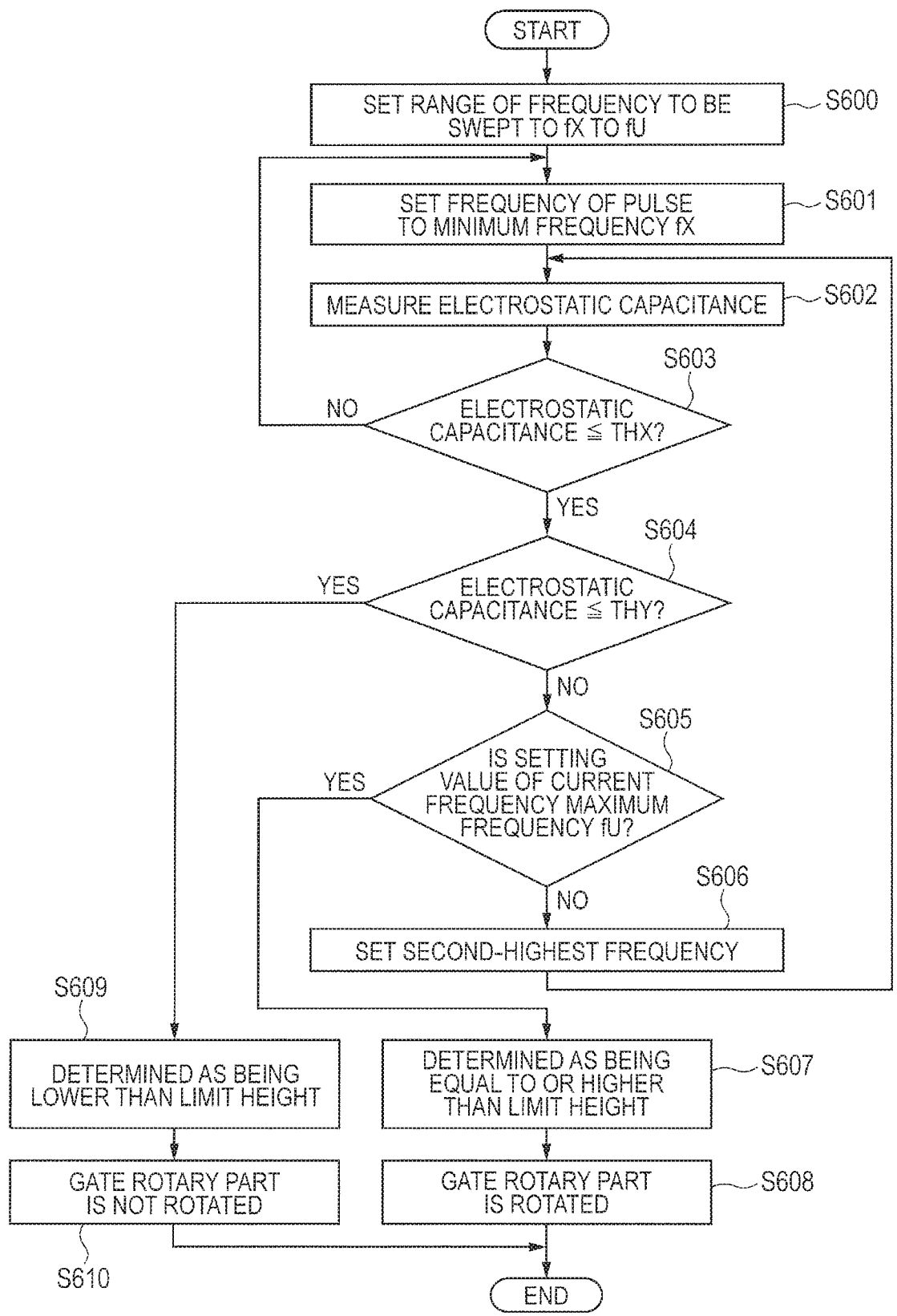
FIG. 20 is a flowchart for showing a control procedure of a rotary gate of an eleventh embodiment.

FIG. 20 is a flowchart for showing a control procedure of the rotary gate of the eleventh embodiment.

In Step S600, the CPU 102 sets the setting range of the frequency of the pulse to be swept to fX to fU. It is assumed that fX is a frequency corresponding to a height slightly shorter than the limit height at which a visitor can enter. It is assumed that fU is a frequency corresponding to a length equal to or shorter than the minimum value of the height of a person, for example, 75 cm.

In Step S601, the CPU 102 sets the frequency of the pulse generated by the variable frequency pulse generator 21 to the minimum frequency fX within the setting range.

In Step S602, the CPU 102 calculates the difference value Ns of the count number Nc1 in the in-phase period with respect to the count number Nc2 in the opposite-phase period as the electrostatic capacitance measured value MC.

In Step S603, when the electrostatic capacitance measured value MC is equal to or smaller than the threshold value THX, the process proceeds to Step S604. When the electrostatic capacitance measured value MC exceeds the threshold value THX, the process returns to Step S601. The threshold value THX is a value to determine whether or not the person to be measured touches the electrode part 301 with the human body. The threshold value THX is a value larger than the measured value of the electrostatic capacitance when the length half the wavelength of the clock CLK1 (the pulse of the variable frequency pulse generator 21) matches the distance from the terminal TR to the ground through the reception electrode TPR and the human body of the person to be measured.

In Step S604, in the case where the electrostatic capacitance measured value MC exceeds the threshold value THY, the process proceeds to Step S605. In the case where the electrostatic capacitance measured value MC is equal to or smaller than the threshold value TY, the process proceeds to Step S609. The threshold value THY is a value obtained by adding a margin to the average value of the measured values of the electrostatic capacitance when the length half the wavelength of the clock CLK1 (the pulse of the variable frequency pulse generator 21) matches the distance from the terminal TR to the ground through the reception electrode TPR and the human body of the person to be measured. Namely, THX>THY is satisfied.

In Step S605, in the case where the currently-set frequency of the pulse is the maximum frequency FU within the setting range, the process proceeds to Step S607. In the case where the currently-set frequency of the pulse is not the maximum frequency FU within the setting range, the process returns to Step S602.

In Step S607, the CPU 102 determines that the height of the person to be measured is equal to or larger than the limit height.

In Step S608, the CPU 102 allows the driving unit 809 to rotate the gate rotary part 803 so that the gate bar 802 is rotated.

In Step S609, the CPU 102 determines that the height of the person to be measured is smaller than the limit height.

In Step S610, the CPU 102 does not allow the driving unit 809 to rotate the gate rotary part 803. Accordingly, the gate bar 802 is not rotated.

As described above, according to the embodiment, it is determined whether or not the height of the person to be measured is equal to or larger than the limit height on the basis of the electrostatic capacitance measured value. Thus, it is not necessary to calculate the height, and opening/closing of the gate can be controlled in a short time. In addition, in the case where the electrostatic capacitance measured value becomes the threshold value THY or smaller during the sweep of the frequency, the measurement of the electrostatic capacitance thereafter is cancelled, and it is determined whether or not the height of the person to be measured is equal to or larger than the limit height. Thus, opening/closing of the gate can be controlled in a shorter time.

Twelfth Embodiment

In the embodiment, the CPU 102 sweeps the range of the frequency equal to or larger than the limit height. In the case where there is a frequency at which the measured mutual capacitance is equal to or smaller than the threshold value THY in the swept range of the frequency, the CPU 102 determines that the height of the person to be measured is equal to or larger than the limit height. In the case where there is not a frequency at which the measured mutual capacitance is equal to or smaller than the threshold value THY in the swept range of the frequency, the CPU 102 determines that the height of the person to be measured is smaller than the limit height.

Figure 21:
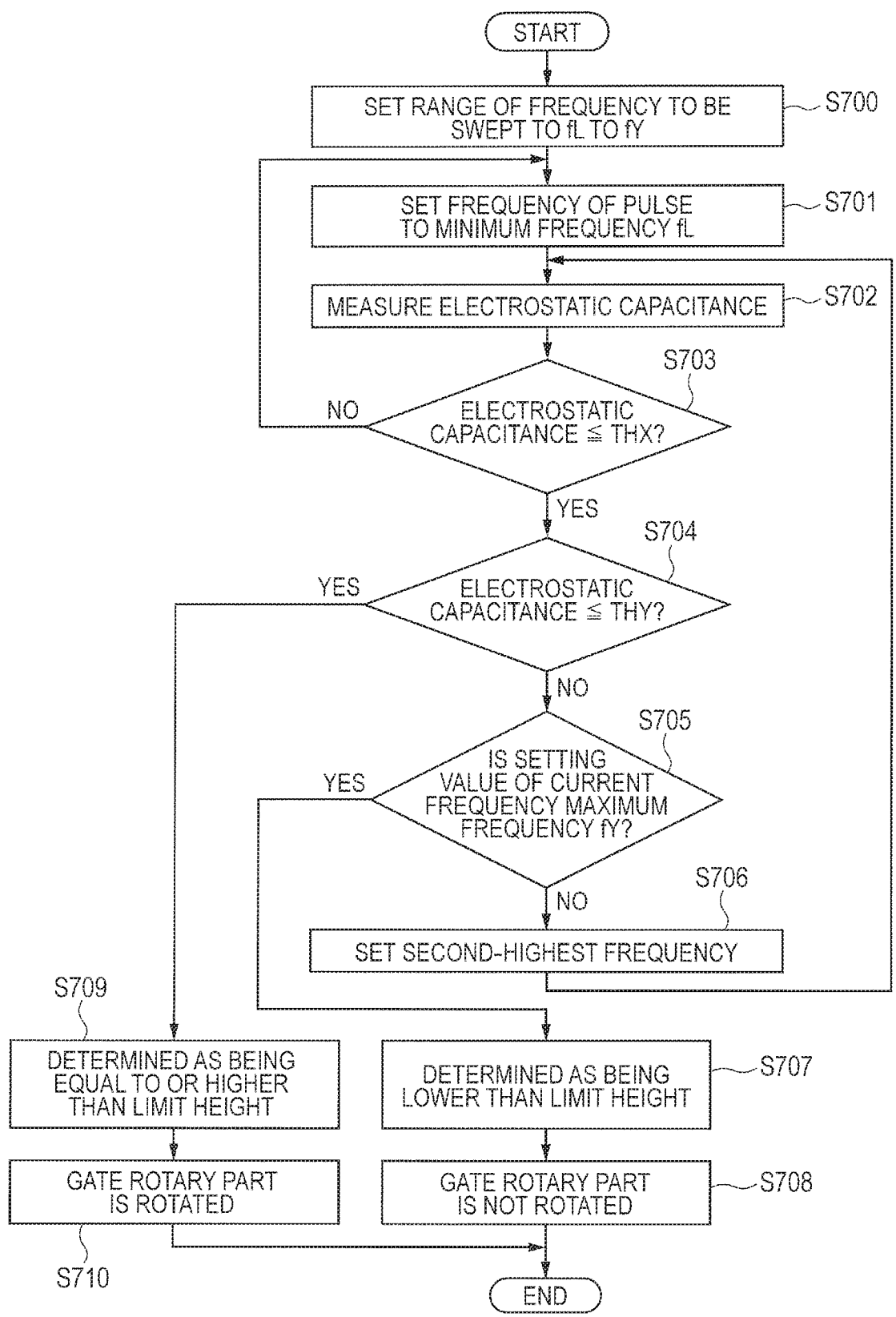
FIG. 21 is a flowchart for showing a control procedure of a rotary gate of a twelfth embodiment.

FIG. 21 is a flowchart for showing a control procedure of the rotary gate of the twelfth embodiment. In Step S701, the CPU 102 sets the setting range of the frequency of the pulse to be swept to fL to fY. It is assumed that fL is a frequency corresponding to a length equal to or larger than the maximum value of the height of a person, for example, 3 m. It is assumed that fY is a frequency corresponding to the limit height at which a visitor can enter.

In Step S701, the CPU 102 sets the frequency of the pulse generated by the variable frequency pulse generator 21 to the minimum frequency fL within the setting range.

In Step S702, the CPU 102 calculates the difference value Ns of the count number Nc1 in the in-phase period with respect to the count number Nc2 in the opposite-phase period as the electrostatic capacitance measured value MC.

In Step S703, in the case where the electrostatic capacitance measured value MC is equal to or larger than the threshold value TY, the process proceeds to Step S704. In the case where the electrostatic capacitance measured value MC is smaller than the threshold value TY, the process proceeds to Step S705.

In Step S704, in the case where the currently-set frequency of the pulse is the maximum frequency FY within the setting range, the process proceeds to Step S706. In the case where the currently-set frequency of the pulse is not the maximum frequency FY within the setting range, the process returns to Step S702.

In Step S705, the CPU 102 determines that the height of the person to be measured is equal to or larger than the limit height, and allows the driving unit 809 to rotate the gate rotary part 803.

In Step S706, the CPU 102 determines that the height of the person to be measured is the limit height, and does not allow the driving unit 809 to rotate the gate rotary part 803.

As described above, according to the embodiment, opening/closing of the gate can be controlled in a short time as similar to the eleventh embodiment.

The invention achieved by the inventors has been concretely described above on the basis of the embodiments. However, it is obvious that the present invention is not limited to the embodiments, and can be variously changed without departing from the scope thereof.

What is claimed is:

1. A height measuring apparatus comprising:
   an electrostatic capacitance sensor that has a transmission electrode and a reception electrode, and measures a mutual capacitance between the transmission electrode and the reception electrode;
   a variable frequency pulse generator that generates a pulse supplied to the transmission electrode; and
   a control apparatus that identifies a frequency at which the measured mutual capacitance becomes a minimum value by allowing the variable frequency pulse generator to sweep the frequency of the pulse and allowing the electrostatic capacitance sensor to measure the mutual capacitance, and obtains a height of a person to be measured on the basis of the identified frequency,
   wherein the control apparatus sets a frequency range within which the frequency of the pulse is to be swept, wherein the frequency range is set to be from a first frequency to a second frequency, wherein the first frequency corresponds to a length equal to or larger than a maximum height of a human body, and wherein the second frequency corresponds to a length equal to or smaller than a minimum height of the human body.

2. The height measuring apparatus according to claim 1, wherein the electrostatic capacitance sensor includes:
   a first terminal that is coupled to the reception electrode;
   a second terminal that is coupled to the transmission electrode;
   a switch circuit that applies a first power supply voltage to the first terminal during a low level of the pulse, and applies a second power supply voltage to the first terminal during a high level of the pulse;
   an output buffer that applies a third power supply voltage to the second terminal during the low level of the pulse and applies the second power supply voltage to the second terminal during the high level of the pulse in an in-phase period, and applies the second power supply voltage to the second terminal during the low level of the pulse and applies the third power supply voltage to the second terminal during the high level of the pulse in an opposite-phase period having the same length as the in-phase period;
   a power supply circuit that supplies the first power supply voltage to the switch circuit, generates a first current to be supplied to the switch circuit, and generates a second current equal to a fixed multiple of the first current;
   a current control oscillation circuit that generates a clock whose frequency is changed in response to the value of the second current supplied from the power supply circuit; and
   a counter that counts a number of clocks in the in-phase period and counts the number of clocks in the opposite-phase period,
   wherein the value of the first current is changed in response to a change in the mutual capacitance between the transmission electrode and the reception electrode, and
   wherein the control apparatus obtains the mutual capacitance between the transmission electrode and the reception electrode on the basis of a difference value between the number of clocks in the in-phase period and the number of clocks in the opposite-phase period.

3. The height measuring apparatus according to claim 1, wherein the control apparatus obtains the height when the minimum value of the mutual capacitance is equal to or smaller than a threshold value.

4. The height measuring apparatus according to claim 1, wherein when the mutual capacitance measured by the electrostatic capacitance sensor is equal to or smaller than a threshold value in an initial value of the frequency of the pulse, the control apparatus sweeps the frequency and measures the mutual capacitance to obtain the height of the person to be measured.

5. The height measuring apparatus according to claim 1, wherein the control apparatus sweeps the frequency of the pulse in a range between 50 MHz to 200 MHz.

6. The height measuring apparatus according to claim 1, wherein the control apparatus obtains the height L on the basis of the following equation (1), $$L = c/(2 \times fm) \qquad (1)$$

where fm is a frequency at which the mutual capacitance becomes the minimum value, and c is the velocity of light.

7. The height measuring apparatus according to claim 2, wherein the control apparatus obtains the height L on the basis of the following equation (2), $$L = c/(2 \times fm) - D \qquad (2)$$

where fm is a frequency at which the mutual capacitance becomes the minimum value, c is the velocity of light, and D is a wiring length from the first terminal to the reception electrode.

8. The height measuring apparatus according to claim 2, wherein the control apparatus obtains a tentative height VL on the basis of the following equation (3) to use a value obtained by multiplying the tentative height by a preliminarily-set ratio as the height, $$VL = c/(2 \times fm) - D \qquad (3)$$

where fm is a frequency at which the mutual capacitance becomes the minimum value, c is the velocity of light, and D is a wiring length from the first terminal to the reception electrode.

9. The height measuring apparatus according to claim 8, wherein the control apparatus uses a ratio on the basis of a human body ratio as the ratio.

10. The height measuring apparatus according to claim 8, wherein the control apparatus uses a value in accordance with an age of the person to be measured as the ratio.

11. The height measuring apparatus according to claim 8, wherein the control apparatus uses a value in accordance with the tentative height as the ratio.

12. A health care device comprising:
   an electrostatic capacitance sensor that has a transmission electrode and a reception electrode, and measures a mutual capacitance between the transmission electrode and the reception electrode;
   a variable frequency pulse generator that generates a pulse supplied to the transmission electrode;
   a control apparatus that identifies a frequency at which the measured mutual capacitance becomes a minimum value by allowing the variable frequency pulse generator to sweep the frequency of the pulse and allowing the electrostatic capacitance sensor to measure the mutual capacitance, and obtains a height of a person to be measured on the basis of the identified frequency, wherein the control apparatus sets a frequency range within which the frequency of the pulse is to be swept, wherein the frequency range is set to be from a first frequency to a second frequency, wherein the first frequency corresponds to a length equal to or larger than a maximum height of a human body, and wherein the second frequency corresponds to a length equal to or smaller than a minimum height of the human body; and
   a pair of hand grips that can be gripped by the person to be measured,
   wherein the transmission electrode and the reception electrode are arranged at one of the pair of hand grips.

13. The health care device according to claim 12, comprising:
   a placement table on which the person to be measured can be placed;
   a plurality of electrodes that is provided on the placement table;
   a plurality of electrodes that is provided at the other of the pair of hand grips; and
   a body composition measuring circuit that measures the body composition of a human body of the person to be measured by a biological impedance method using some or all of the electrodes provided on the placement table, the electrodes provided at the other of the pair of hand grips, the transmission electrode, and the reception electrode.

14. The health care device according to claim 12, comprising a weight sensor for measuring the weight of the person to be measured,
   wherein the control apparatus obtains the BMI (Body Mass Index) of the person to be measured on the basis of the measured height and the measured weight.

15. A rotary gate comprising:
   an electrostatic capacitance sensor that has a transmission electrode and a reception electrode, and measures a mutual capacitance between the transmission electrode and the reception electrode;
   a variable frequency pulse generator that generates a pulse supplied to the transmission electrode;
   a control apparatus that obtains the measured mutual capacitance by allowing the variable frequency pulse generator to sweep the frequency of the pulse and allowing the electrostatic capacitance sensor to measure the mutual capacitance, wherein the control apparatus sets a frequency range within which the frequency of the pulse is to be swept, wherein the frequency range is set to be from a first frequency to a second frequency, wherein the first frequency corresponds to a length equal to or larger than a maximum height of a human body, and wherein the second frequency corresponds to a length equal to or smaller than a minimum height of the human body; and
   a gate bar that is movable in a rotatable manner,
   wherein the transmission electrode and the reception electrode are provided at the gate bar, and
   wherein the control apparatus controls the rotation of the gate bar on the basis of the measured mutual capacitance.

\* \* \* \* \*